(12) United States Patent
Gysling et al.

(10) Patent No.: US 7,134,320 B2
(45) Date of Patent: *Nov. 14, 2006

(54) APPARATUS AND METHOD FOR PROVIDING A DENSITY MEASUREMENT AUGMENTED FOR ENTRAINED GAS

(75) Inventors: Daniel L. Gysling, Glastonbury, CT (US); Patrick Curry, Glastonbury, CT (US); Douglas H. Loose, Southington, CT (US); Thomas E. Banach, Barkhamsted, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/909,593

(22) Filed: Aug. 2, 2004

(65) Prior Publication Data

US 2005/0061060 A1  Mar. 24, 2005

Related U.S. Application Data

(63) Continuation-in-part of application No. 10/892,886, filed on Jul. 15, 2004.

(60) Provisional application No. 60/487,832, filed on Jul. 15, 2003, provisional application No. 60/548,215, filed on Feb. 27, 2004, provisional application No. 60/571,903, filed on May 17, 2004, provisional application No. 60/579,448, filed on Jun. 14, 2004, provisional application No. 60/570,321, filed on May 12, 2004, provisional application No. 60/539,640, filed on Jan. 28, 2004, provisional application No. 60/524,964, filed on Nov. 25, 2003, provisional application No. 60/512,794, filed on Oct. 20, 2003, provisional application No. 60/510,302, filed on Oct. 10, 2003, provisional application No. 60/504,785, filed on Sep. 22, 2003, provisional application No. 60/503,334, filed on Sep. 16, 2003, provisional application No. 60/491,860, filed on Aug. 1, 2003.

(51) Int. Cl.
*G01N 9/00* (2006.01)
*G01N 33/00* (2006.01)
*G01F 1/20* (2006.01)

(52) U.S. Cl. .................. 73/32 A; 73/861.18; 73/61.44

(58) Field of Classification Search ............... 73/61.44, 73/61.45, 61.47, 61.49, 61.78, 61.79, 861.04, 73/861.08, 32 A, 861.18
See application file for complete search history.

(56) References Cited

U.S. PATENT DOCUMENTS

| | | | |
|---|---|---|---|
| 2,874,568 A | 12/1955 | Petermann | |
| 3,444,723 A * | 5/1969 | Wakefield | 73/32 A |
| 3,780,577 A * | 12/1973 | Brown | 73/861.28 |
| 4,004,461 A | 1/1977 | Lynworth | |
| 4,048,853 A | 9/1977 | Smith et al. | 73/861.25 |
| 4,080,837 A | 3/1978 | Alexander et al. | 73/61.45 |
| 4,144,754 A * | 3/1979 | Pitts et al. | 73/861.02 |
| 4,195,517 A | 4/1980 | Kalinoski et al. | |
| 4,248,085 A | 2/1981 | Coulthard | 73/861.06 |
| 4,262,523 A * | 4/1981 | Stansfeld | 73/24.05 |
| 4,445,389 A | 5/1984 | Potzick et al. | 73/861.27 |
| 4,580,444 A * | 4/1986 | Abts et al. | 73/61.75 |
| 4,773,257 A * | 9/1988 | Aslesen et al. | 73/61.44 |
| 4,823,613 A * | 4/1989 | Cage et al. | 73/861.355 |
| 4,896,540 A | 1/1990 | Shakkottai et al. | 73/861.02 |
| 5,029,482 A * | 7/1991 | Liu et al. | 73/861.04 |
| 5,040,415 A | 8/1991 | Barkhoudarian | 73/861.03 |
| 5,083,452 A | 1/1992 | Hope | 73/61 R |
| 5,218,197 A | 6/1993 | Carroll | 250/227.19 |
| 5,224,372 A | 7/1993 | Kolpak | |
| 5,259,239 A * | 11/1993 | Gaisford | 73/61.44 |
| 5,285,675 A | 2/1994 | Colgate et al. | 73/23.2 |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,594,180 A * | 1/1997 | Carpenter et al. | 73/861.356 |
| 5,654,502 A * | 8/1997 | Dutton | 73/152.18 |
| 5,741,980 A | 4/1998 | Hill et al. | 73/861.04 |
| 5,770,805 A | 6/1998 | Castel | 73/861.04 |

| | | | |
|---|---|---|---|
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,856,622 A | 1/1999 | Yamamoto et al. | |
| 5,948,959 A | 9/1999 | Peloquin | 73/1.83 |
| 6,016,702 A | 1/2000 | Maron | |
| 6,065,328 A * | 5/2000 | Dayton et al. | 73/25.01 |
| 6,151,958 A | 11/2000 | Letton et al. | 73/61.79 |
| 6,202,494 B1 | 3/2001 | Ricbel et al. | 73/861.29 |
| 6,318,156 B1 * | 11/2001 | Dutton et al. | 73/61.44 |
| 6,335,959 B1 | 1/2002 | Lynch et al. | 378/45 |
| 6,354,147 B1 * | 3/2002 | Gysling et al. | 73/61.79 |
| 6,378,357 B1 | 4/2002 | Han et al. | 73/54.41 |
| 6,397,683 B1 | 6/2002 | Hagenmeyer et al. | |
| 6,401,538 B1 * | 6/2002 | Han et al. | 73/599 |
| 6,422,092 B1 * | 7/2002 | Morrison et al. | 73/861.04 |
| 6,435,030 B1 | 8/2002 | Gysling et al. | 73/587 |
| 6,450,037 B1 | 9/2002 | Davis et al. | |
| 6,463,813 B1 | 10/2002 | Gysling | 73/862.59 |
| 6,502,465 B1 * | 1/2003 | Vedapuri et al. | 73/861.04 |
| 6,502,466 B1 * | 1/2003 | Cage et al. | 73/861.355 |
| 6,532,827 B1 | 3/2003 | Ohnishi | |
| 6,536,291 B1 | 3/2003 | Gysling et al. | 73/861.42 |
| 6,550,342 B1 | 4/2003 | Croteau et al. | 73/800 |
| 6,575,043 B1 * | 6/2003 | Huang et al. | 73/861.25 |
| 6,587,798 B1 | 7/2003 | Kersey et al. | 702/50 |
| 6,672,163 B1 * | 1/2004 | Han et al. | 73/597 |
| 6,698,297 B1 | 3/2004 | Gysling | |
| 6,745,135 B1 * | 6/2004 | Keilty et al. | 702/45 |
| 6,763,698 B1 * | 7/2004 | Greenwood | 73/30.01 |
| 6,802,224 B1 * | 10/2004 | Nakao et al. | 73/861.354 |
| 6,817,229 B1 * | 11/2004 | Han et al. | 73/64.53 |
| 6,837,098 B1 | 1/2005 | Gysling et al. | |
| 6,945,095 B1 * | 9/2005 | Johansen | 73/61.45 |
| 6,950,760 B1 | 9/2005 | Henry et al. | |
| 6,971,259 B1 | 12/2005 | Gysling | |
| 7,059,199 B1 | 6/2006 | Mattar et al. | 73/861.356 |
| 2001/0045134 A1 * | 11/2001 | Henry et al. | 73/861.356 |
| 2003/0089161 A1 | 5/2003 | Gysling | |
| 2004/0069069 A1 | 4/2004 | Croteau | |
| 2004/0074312 A1 * | 4/2004 | Gysling | 73/861.04 |
| 2004/0139791 A1 * | 7/2004 | Johansen | 73/61.44 |
| 2004/0144182 A1 | 7/2004 | Gysling et al. | |
| 2004/0167735 A1 | 8/2004 | Gysling et al. | |
| 2004/0168522 A1 * | 9/2004 | Fernald er al. | 73/861.01 |
| 2004/0194539 A1 | 10/2004 | Gysling | |
| 2004/0199340 A1 | 10/2004 | Gysling et al. | |
| 2004/0199341 A1 | 10/2004 | Gysling et al. | |
| 2004/0210404 A1 | 10/2004 | Gysling et al. | |
| 2004/0216509 A1 * | 11/2004 | Antonijevic | 73/1.16 |
| 2004/0226386 A1 | 11/2004 | Croteau et al. | |
| 2004/0231431 A1 | 11/2004 | Bailey et al. | |
| 2004/0255695 A1 | 12/2004 | Gysling et al. | |
| 2005/0011284 A1 | 1/2005 | Davis et al. | |
| 2005/0039520 A1 | 2/2005 | Bailey et al. | |
| 2005/0044966 A1 | 3/2005 | Croteau et al. | |
| 2005/0050956 A1 | 3/2005 | Croteau et al. | |
| 2005/0061060 A1 | 3/2005 | Banach et al. | |
| 2005/0072216 A1 * | 4/2005 | Engel | 73/53.01 |
| 2005/0120799 A1 * | 6/2005 | Gysling et al. | 73/753 |
| 2005/0138993 A1 * | 6/2005 | Mattar et al. | 73/61.78 |
| 2005/0171710 A1 | 8/2005 | Gysling et al. | |
| 2005/0188771 A1 * | 9/2005 | Lund et al. | 73/861 |
| 2005/0193832 A1 * | 9/2005 | Tombs et al. | 73/861 |
| 2005/0210965 A1 * | 9/2005 | Sinha | 73/61.79 |

FOREIGN PATENT DOCUMENTS

| | | | |
|---|---|---|---|
| EP | 222503 A1 * | 5/1987 | |
| EP | 253504 A1 * | 1/1988 | |
| GB | 2009931 | 6/1979 | |

OTHER PUBLICATIONS

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research, The Parametric Approach", H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attenuation of Acoustic Waves in Suspensions" by R.L. Gibson, Jr. and M.N. Toksoz.

"PVDF and Array Transducers" Author: Robert A. Day—NDTnet—Sep. 1996—vol. No. 9.

"Polymer Piezoelectric Transducers for Ultrasonic NDE" Aughors: Yoseph Bar-Cohen, Tianji Xue and Shyh-Shiuh Lih.

"Piezoelectric Polymers" ICASE Report No. 2001-43—Dec. 2001.

"Piezo Film Sensors Technical Manual" P/N 1005663-1 Rev. B Apr. 2, 1999.

Sonar-Based Volumetric Flow Meter For Pulp and Paper Applications—Daniel L. Gysling & Douglas H. Loose—Dec. 13, 2003.

Sonar-Based Volumetric Flow Meter for Chemical and Petrochemical Applications—Daniel L. Gysling & Douglas H. Loose—Feb. 14, 2003.

New Flowmeter Principle—By Walt Boyes—Flow Control Magazine—Oct. 2003 Issue.

SONAR Gets into the Flow—Daniel L. Gysling and Douglas H. Loose—Modern Process—Jan. 2004.

U.S. Appl. No. 60/445,795, filed Feb. 2003, Mattar et al.
U.S. Appl. No. 60/452,934, filed Mar. 2003, Mattar et al.
U.S. Appl. No. 60/549,161, filed Mar. 2004, Lansangan.

* cited by examiner

*Primary Examiner*—Hezron Williams
*Assistant Examiner*—John Fitzgerald

(57) ABSTRACT

A flow measuring system combines a density measuring device and a device for measuring the speed of sound (SOS) propagating through the fluid flow and/or for determining the gas volume fraction (GVF) of the flow. The GVF meter measures acoustic pressures propagating through the fluids to measure the speed of sound $\alpha_{mix}$ propagating through the fluid to calculate at least gas volume fraction of the fluid and/or SOS. In response to the measured density and gas volume fraction, a processing unit determines the density of non-gaseous component of an aerated fluid flow. For three phase fluid flows, the processing unit can determine the phase fraction of the non-gaseous components of the fluid flow. The gas volume fraction (GVF) meter may include a sensing device having a plurality of strain-based or pressure sensors spaced axially along the pipe for measuring the acoustic pressures propagating through the flow.

32 Claims, 20 Drawing Sheets

APPARATUS AND METHOD FOR PROVIDING A DENSITY MEASUREMENT AUGMENTED FOR ENTRAINED GAS

CROSS-REFERENCE TO RELATED APPLICATIONS

The present invention is a continuation-in-part of U.S. patent application Ser. No. 10/892,886 filed Jul. 15, 2004, which claimed the benefit of U.S. Provisional Patent Application No. 60/487,832 filed Jul. 15, 2003, and claims the benefit of U.S. Provisional Patent Application No. 60/548,215 filed Feb. 27, 2004, U.S. Provisional Patent Application No. 60/571,903 filed May 17, 2004, U.S. Provisional Patent Application No. 60/579,448 filed Jun. 14, 2004, U.S. Provisional Patent Application No. 60/570,321 filed May 12, 2004, U.S. Provisional Patent Application No. 60/539,640 filed Jan. 28, 2004, U.S. Provisional Patent Application No. 60/524,964 filed Nov. 25, 2003, U.S. Provisional Patent Application No. 60/512,794 filed Oct. 20, 2003, U.S. Provisional Patent Application No. 60/510,302 filed Oct. 10, 2003, U.S. Provisional Patent Application No. 60/504,785 filed Sep. 22, 2003, U.S. Provisional Patent Application No. 60/503,334 filed Sep. 16, 2003, U.S. Provisional Patent Application No. 60/491,860 filed Aug. 1, 2003, which are all incorporated herein by reference.

TECHNICAL FIELD

This invention relates to an apparatus for measuring the density of a fluid flow having entrained gas therein, and more particularly to an apparatus that measures the speed of sound propagating through the flow to determine the gas volume fraction of the flow in the process to augment or correct the density measurement of a density meter and/or to provide a composition measurement compensated for entrained gas.

BACKGROUND ART

Density meters are commonly used instruments in industrial processes. Common types of density meters include nuclear densitometers, vibrating vane densitometers and Coriolis flow meters having a density measurement as a by-product measurement.

In most applications, density measurements are used to discern bulk properties of the process fluid. Typically, density measurements are intended to provide information about the liquid and solid phases of a process fluid. These measurements get confound when an unknown amount of entrained air is present.

For a two-component mixture, knowing the component densities and accurately measuring the mixture density provides a means to determine the phase fractions of each of the two components. However, the presence of a third phase, such as entrained air (or gas) confounds this relationship. Typically, there is not significant contrast in the densities of the liquid components, which results in large errors in phase fraction determination resulting from small levels of entrained air.

The measurement of slurries used in the paper and pulp industries and in other industries particularly presents problems in the production of paper. Slurries commonly used in the paper and pulp industry are mostly water and typically contain between 1% and 10% pulp content by mass. Monitoring the gas volume fraction of a slurry can lead to improved quality and efficiency of the paper production process.

Processes run in the paper and pulp industry can often, either intentionally or unintentionally, entrain gas/air. Typically, this entrained air results in measurement errors in process monitoring equipment such as density meters. Industry estimates indicate that entrained air levels of 2–4% are common. Since most density meters are unable to distinguish between air and liquid, interpreting their output as a density measurement or composition measurement would result in an overestimate of the density of the liquid or slurry present at the measurement location. Similarly, the void fraction of the air within the pipe can cause errors in compositional measurements.

Thus, providing a method and apparatus for measuring entrained air in paper and pulp slurries, for example, would provide an accurate measurement of the entrained air and would provide a means to correct the output of density meters.

As suggested, multiphase process flow rate is a critical process control parameter for the paper and pulp industry. Knowing the amounts of liquid, solids and entrained gases flowing in process lines is key to optimizing the overall the papermaking process. Unfortunately, significant challenges remain in the achieving accurate, reliable, and economical monitoring of multiphase flow rates of paper and pulp slurries. Reliability challenges arise due the corrosive and erosive properties of the slurry. Accuracy challenges stem from the multiphase nature of the slurries. Economical challenges arise from the need to reduce total lifetime cost of flow measurement, considering installation and maintenance costs in addition to the initial cost of the equipment.

Currently, there is an unmet need for multiphase flow measurement in the processing industry, such as the paper and pulp industry. Real time flow measurement is typically restricted to monitoring the total volumetric flow rate in a process line without providing information on the composition of the process mixture.

Similarly, well head monitoring represents a difficult technical challenge with the presence of entrained gas. Metering well head production rates is a long standing challenge for the oil and gas industry. Performing accurate and timely monitoring of the production rates has many benefits, which include optimizing overall field and specific well production. The difficulty is due in no small part to the extreme variability of produced fluids which can include various types and mixtures of oil, water, gas, and solid particles.

Many companies have developed various types of three phase meters designed to address the well head flow metering market. These products have met relatively limited commercial success due to a combination of performance, accuracy, and cost issues. This disclosure provide an means and apparatus for well head monitoring that combines multiple existing technologies in to system that should meet a wide range of cost and performance goals.

It is proposed herein to use sonar-based entrained gas measurement to determine the entrained gas level in conjunction with any mixture density measurement to improve the accuracy and therefore value of the density measurement. A sound speed based entrained gas measurement can accurately determine the entrained gas in an aerated mixture without precise knowledge of the composition of either the non-gas components of the multiphase mixture of the composition of gas itself. Thus, the entrained gas levels can be determined essentially independent of the determination of the liquid properties. The accuracy could be improved using the sound speed measurement and mixture density simultaneously, but is not required. Determining the entrained gas level enables the density measurement to determine the properties of non-gas component of the multiphase mixture with the same precision as if the gas was not present. This capability also enables the density meters to provide significantly enhanced compositional information for aerated mixtures.

SUMMARY OF THE INVENTION

Objects of the present invention include an apparatus having a device for determining the speed of sound propagating within a fluid flow in a pipe to determine the gas volume fraction of a process fluid or flow flowing within a pipe, and augment to improve the accuracy of a density measurement of a density meter and/or to provide a composition measurement compensated for entrained gas.

According to the present invention, a flow measuring system for determining the density of a fluid flowing in a pipe is provided. The measuring system comprises a density meter that provides a density signal indicative of the density of the fluid flowing in the pipe. A flow measuring device measures the speed of sound propagating through the fluid. The measuring device provides an SOS signal indicative of the speed of sound propagating through the fluid and/or a GVF signal indicative of the gas volume fraction of the fluid. A processing unit determines the density of the non-gaseous component of the aerated fluid in response to the SOS signal and/or the GVF signal and the density signal.

According to the present invention, a well head metering system for measuring density of non-gaseous components of a three phase fluid flowing in a pipe is provided. The metering system comprises a density meter that provides a density signal indicative of the density of the fluid flowing in the pipe. A flow measuring device measures the speed of sound propagating through the fluid. The measuring device provides an SOS signal indicative of the speed of sound propagating through the fluid and/or a GVF signal indicative of the gas volume fraction of the fluid. A processing unit determines the density of the non-gaseous component of the aerated fluid in response to the SOS signal and/or the GVF signal and the density signal.

The foregoing and other objects, features and advantages of the present invention will become more apparent in light of the following detailed description of exemplary embodiments thereof.

BEST MODE FOR CARRYING OUT THE INVENTION

Density meters 16 provide a measurement of the density of a fluid flow 12 passing through a pipe 14. As described in detail hereinbefore, a density meter provides erroneous density measurements in the presence of entrained gas (e.g., bubbly gas) within the fluid flow. The present invention provides a means for augmenting or compensating the density meter to determine improved density measurements that provides the density of the non-gas portion of the fluid flow 12. The density meter may be any device capable of measuring the density of the fluid flow, such as nuclear densitometers, vibrating vane densitometers and Coriolis flow meters, which provide a density measurement as a by-product measurement.

The present invention proposes the use of sonar-based entrained gas measurements to determine the entrained gas level in conjunction with any density measurement of a mixture flowing in a pipe to improve the accuracy, and therefore value of the density measurement. A sound speed based entrained gas measurement can accurately determine the entrained gas in an aerated mixture without precise knowledge of the composition of either the non-gas components of the multiphase mixture or the composition of gas itself. Thus, the entrained gas levels can be determined essentially independent of the determination of the liquid properties. The accuracy could be improved using the sound speed measurement and mixture density simultaneously, but is not required. Determining the entrained gas level enables the density measurement to determine the properties of non-gas component of the multiphase mixture with the same precision as if the gas was not present. This capability also enables the density meters to provide significantly enhanced compositional information for aerated mixtures.

Figure 1:
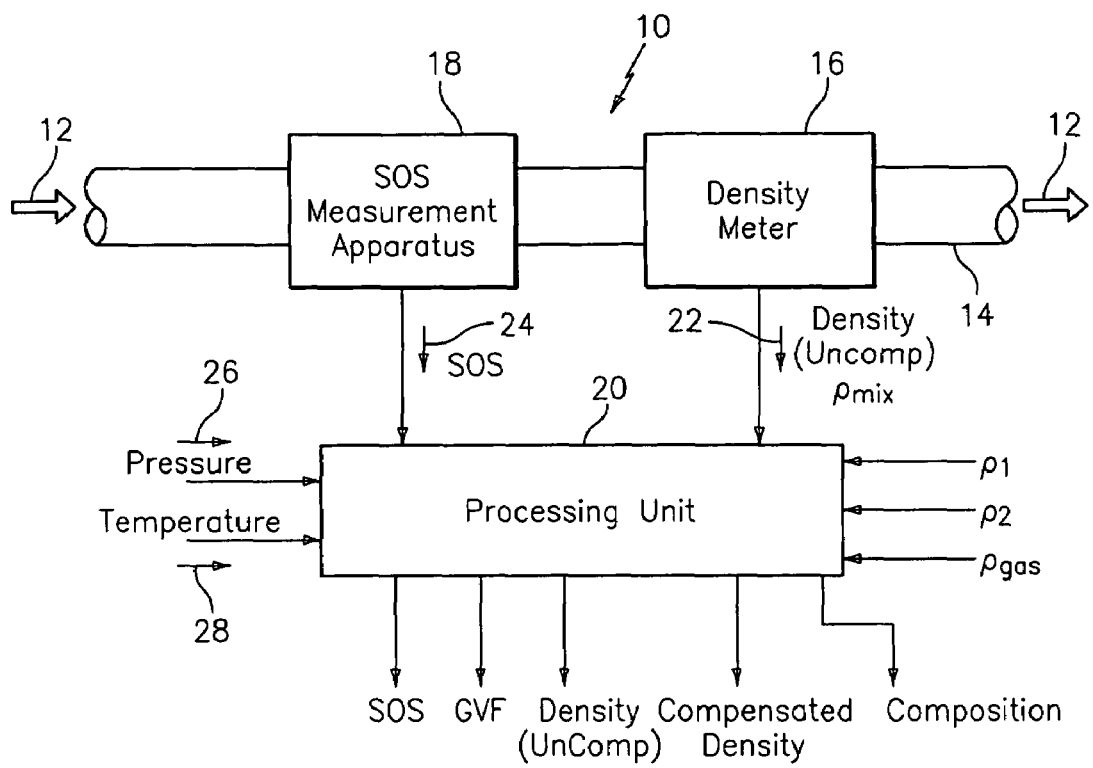
FIG. 1 is a schematic illustration of a flow measuring system for providing a density and/or composition measurement augmented for entrained gas within an aerated fluid flow passing within a pipe, in accordance with the present invention.

As shown in FIG. 1, one embodiment of a flow measuring system 10 embodying the present invention includes a density meter 16, a speed of sound (SOS) measuring apparatus 18 and a processing unit 20 to provide any one or more of the following parameters of the fluid flow 12, namely, gas volume fraction, speed of sound propagating through the fluid flow, uncompensated density, compensated density and composition. The fluid flow may be any aerated fluid or mixture including liquid, slurries, solid/liquid mixture, liquid/liquid mixture, solid/solid mixture and any other multiphase flow having entrained gas.

In this embodiment, the density meter 16 provides a signal 22 indicative of the density of the fluid flow 12 not augmented or compensated for entrained gas. The SOS measuring apparatus 18 provides an SOS signal 24 indicative of the speed of sound propagating through the fluid flow. A processing unit 20 determines at least one of the parameters of the fluid flow described hereinbefore in response to the SOS signal 24 and density signal 22. Pressure and/or temperature signals 26,28 may also be provided to the processing unit 20, which may be used to provide more accurate measurements of the gas volume fraction. The pressure and temperature may be measured by known means or estimated.

The SOS measuring device 18 includes any means for measuring the speed of sound propagating through the aerated flow 12. One method includes a pair of ultra-sonic sensors axially spaced along the pipe 14, wherein the time of flight of an ultrasonic signal propagating between an ultra-sonic transmitter and receiver is indicative of the speed of sound. Depending on the characteristics of the flow, the frequency of the ultra-sonic signal must be relating low to reduce scatter within the flow. The meter is similar as that described in U.S. patent application Ser. No. 10/756,922 filed on Jan. 13, 2004, which is incorporated herein by reference.

Figure 2:
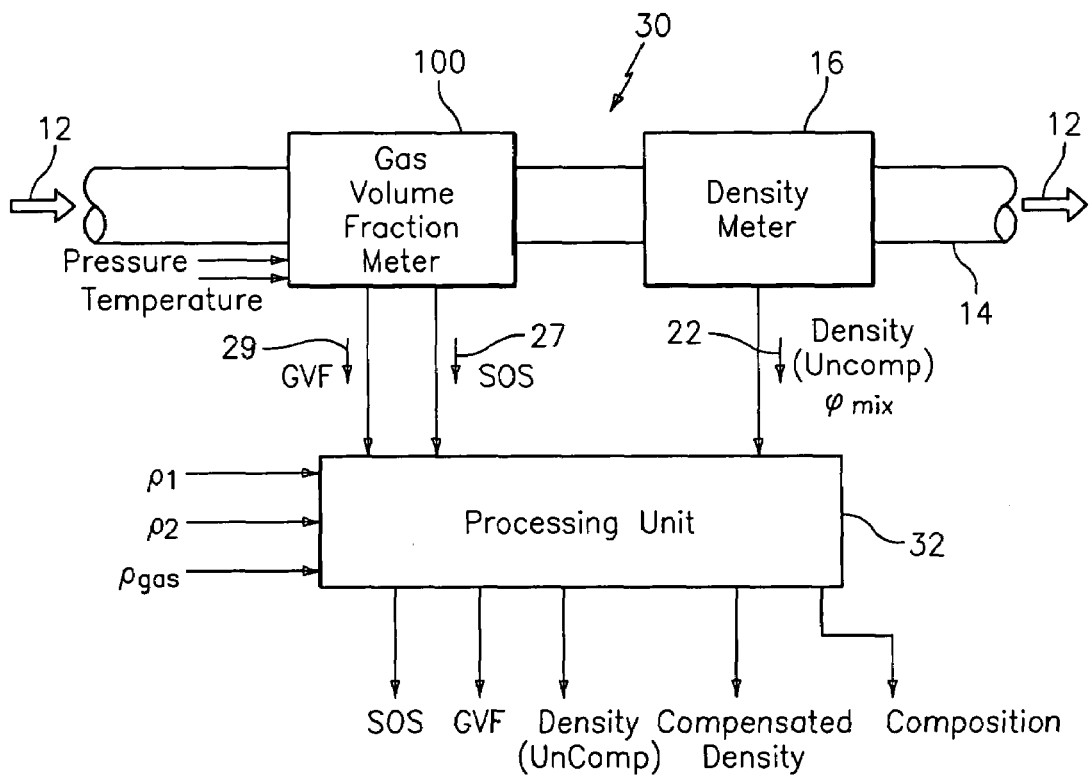
FIG. 2 is a schematic illustration of another flow measuring system for providing a density and/or composition measurement augmented for entrained gas within an aerated fluid flow passing within a pipe, in accordance with the present invention.
Figure 7:
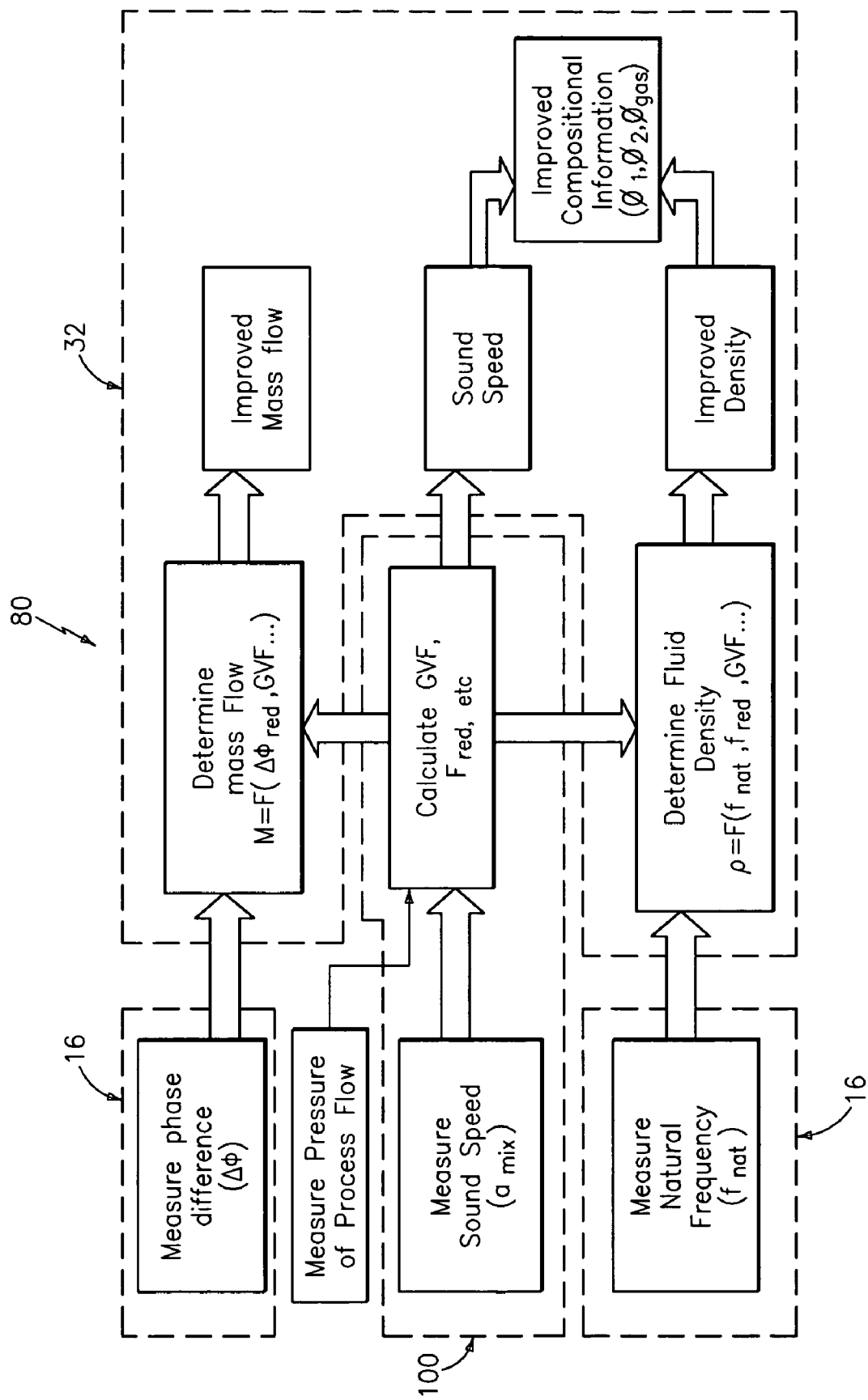
FIG. 7 is a function block diagram of a processing unit of flow measuring system similar to that of FIG. 6, in accordance with the present invention.
Figure 11:
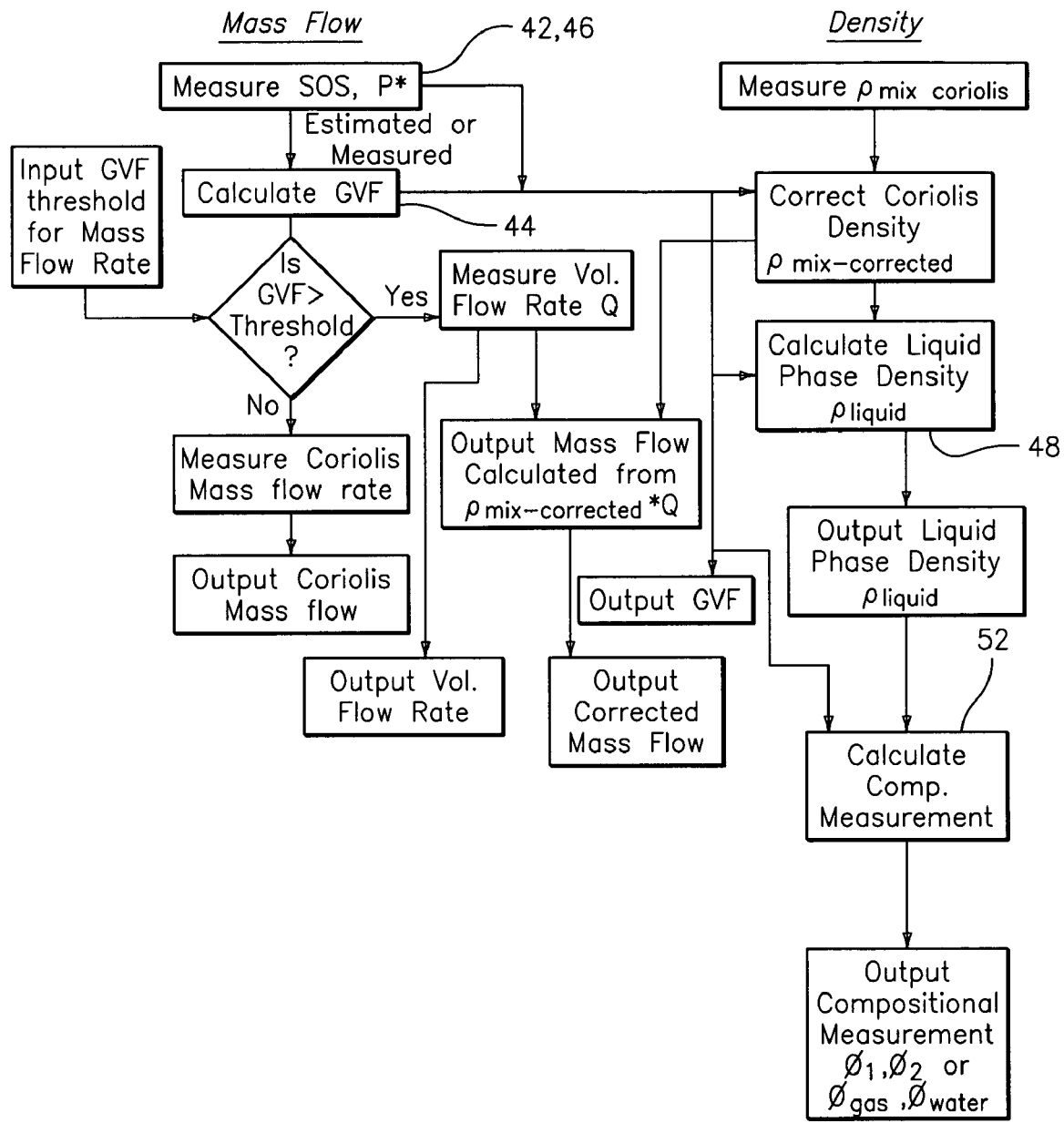
FIG. 11 is another embodiment of a function block diagram of a processing unit of flow measuring system similar to that of FIG. 7, in accordance with the present invention.

Alternatively, a flow measuring system 30 embodying the present invention, as shown in FIGS. 2, 7 and 11, provides a gas volume fraction (GVF) meter 100 for determining the gas volume fraction of the fluid flow 12, which will be described in greater detail hereinafter. The GVF meter 100 comprises a sensing device 116 having a plurality of strain-based or pressure sensors 118–121 spaced axially along the pipe for measuring the acoustic pressures 190 propagating through the flow 12. The GVF meter determines and provides a first signal 27 indicative of the SOS propagating through the fluid flow 12 and a second signal 29 indicative of the gas volume fraction (GVF) of the flow 12, which will be described in greater detail hereinafter. The gas volume fraction meter 100 is similar to that described in U.S. patent application Ser. No. 10/762,410 filed on Jan. 21, 2004, which is incorporated herein by reference. The processing unit 32 determines at least one of the parameters of the fluid flow described hereinbefore in response to the SOS signal 24 and/or GVF signal 29, and the density signal 22.

Figure 3:
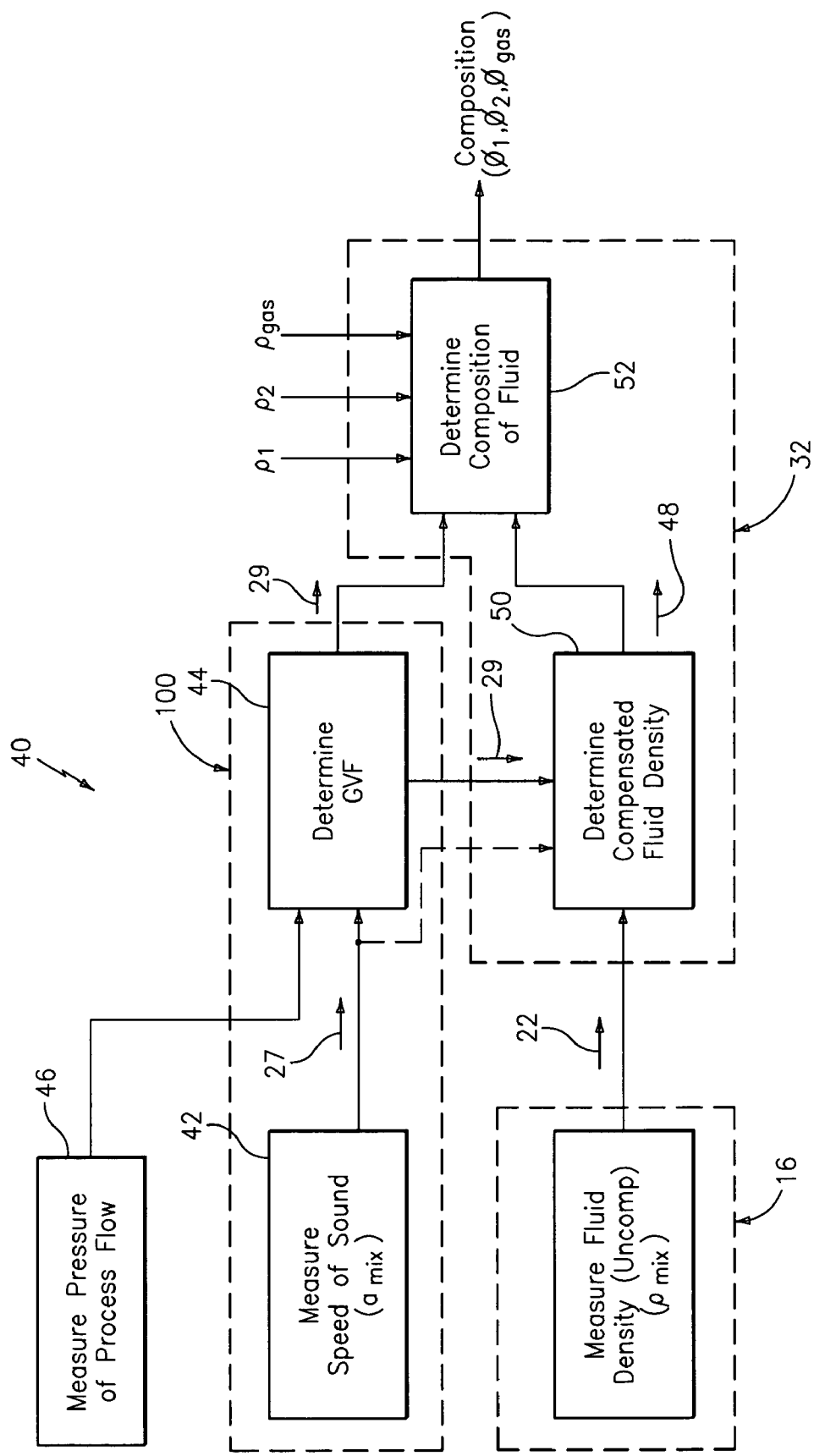
FIG. 3 is a function block diagram of a processing unit of flow measuring system similar to that of FIG. 1, in accordance with the present invention.

FIG. 3 illustrates a functional block diagram 40 of the flow measuring system 30 of FIG. 2. As shown, the GVF meter 100 measures acoustic pressures propagating through the fluids 12, thereby measuring the speed of sound $a_{mix}$ propagating through the fluid flow 12 at 42. The GVF meter 100 calculates the gas volume fraction of the fluid using the measured speed of sound at 44. The GVF meter may also use the pressure of the process flow to determine the gas volume fraction. The pressure may be measured or estimated at 46.

For determining an improved density 48 (i.e., density of non-gas portion of flow 12), the calculated gas volume fraction 29 is provided to the processing unit 32. Knowing the gas volume fraction 29 (and/or speed of sound 27 propagating through the flow) and the measured density 22, the processing unit 32 can determine density of the non-gas portion of the multiphase flow 12.

Specifically, the density ($\rho_{mix}$) 22 of an aerated flow 12 is related to the volumetric phase fraction of the components ($\varnothing_i$) and the density of the components ($\rho_i$).

$$\rho_{mix} = \sum_{i=1}^{N} \phi_i \rho_i$$

Where continuity requires:

$$\sum_{i=1}^{N} \phi_i = 1$$

For example, for a two-component fluid flow:

$$\rho_{mix} = \rho_{nongas}\phi_{nongas} + \rho_{gas}\phi_{gas}$$

therefore, $\rho_{nongas} = (\rho_{mix} - \rho_{gas}\phi_{gas})/\phi_{nongas} = (\rho_{mix} - \rho_{gas}\phi_{gas})/1-\phi_{gas}$, wherein $\phi_{nongas} = 1 - \phi_{gas}$ Assuming the density of the gas ($\rho_{gas}$) is substantially less than the density of the non-gas portion ($\rho_{nongas}$) of the fluid flow 12, the equation can be reduced to:

$$\rho_{nongas} = \rho_{mix}/(1-\phi_{gas})$$

wherein $\rho_{mix}$ is the density of the mixture, $\rho_{nongas}$, $\varnothing_{nongas}$ are the density and phase fraction, respectively, of a non-gas component of the fluid flow, and $\rho_{gas}$, $\varnothing_{gas}$ are the density and phase fraction, respectively, of the entrained gas within the mixture.

Therefore, knowing the density ($\rho_{gas}$) of the gas/air, the measured gas volume fraction of the gas ($\varnothing_{gas}$), and the improved density measurement ($\rho_{mix}$) of the aerated flow to be compensated for entrained gas enable the density ($\rho_{nongas}$) of the non-gas portion of the aerated flow 12 to be determined, which provides improved compositional information of the aerated flow 12. For instances when the density of the gas component is substantially greater than the non-gas component, knowing just the measured density ($\rho_{mix}$) 22 of the aerated flow 12 density of the gas component and the gas volume fraction ($\emptyset_{gas}$) 29 is sufficient to determine the density ($\rho_{nongas}$) 48 of the non-gas component of the flow 12.

The present invention further contemplates determining improved compositional information of the aerated flow 12.

When a two-component mixture 12 includes a third component of entrained gas or gas, the relationship is as follows:

$$\rho_{mix} = \rho_1\phi_1 + \rho_2\phi_2 + \rho_{gas}\phi_{gas}$$

therefore, $\phi_1 = [\rho_{mix} - \rho_{gas}\phi_{gas} - \rho_2(1-\phi_{gas})]/(\rho_1-\rho_2)$, where $\phi_2 = 1 - \phi_1 - \phi_{gas}$ assuming the density of the gas ($\rho_{gas}$) is substantially less than the density of the non-gas portion ($\rho_{nongas}$) of the fluid flow 12, the equation can be reduced to:

$$\phi_1 = [\rho_{mix} - \rho_2(1-\phi_{gas})]/(\rho_1-\rho_2)$$

Therefore, knowing the density ($\rho_{gas}$) of the gas/air and the measured density of the gas volume fraction ($\emptyset_{gas}$) enables density measurement ($\rho_{mix}$) of the mixture to be compensated for entrained gas and provide a density measurement of only the two-component mixture that does not include the density of the entrained air/gas at 50.

Furthermore, knowing the densities of each of the components of the mixture ($\rho_1$, $\rho_2$) and the density of the gas/air ($\rho_{gas}$), and knowing the measured densities of the mixture ($\rho_{mix}$) and gas volume fraction ($\emptyset_{gas}$) enable the volume fraction of each component ($\emptyset_1$, $\emptyset_2$) to be determined at 52.

Figure 4:
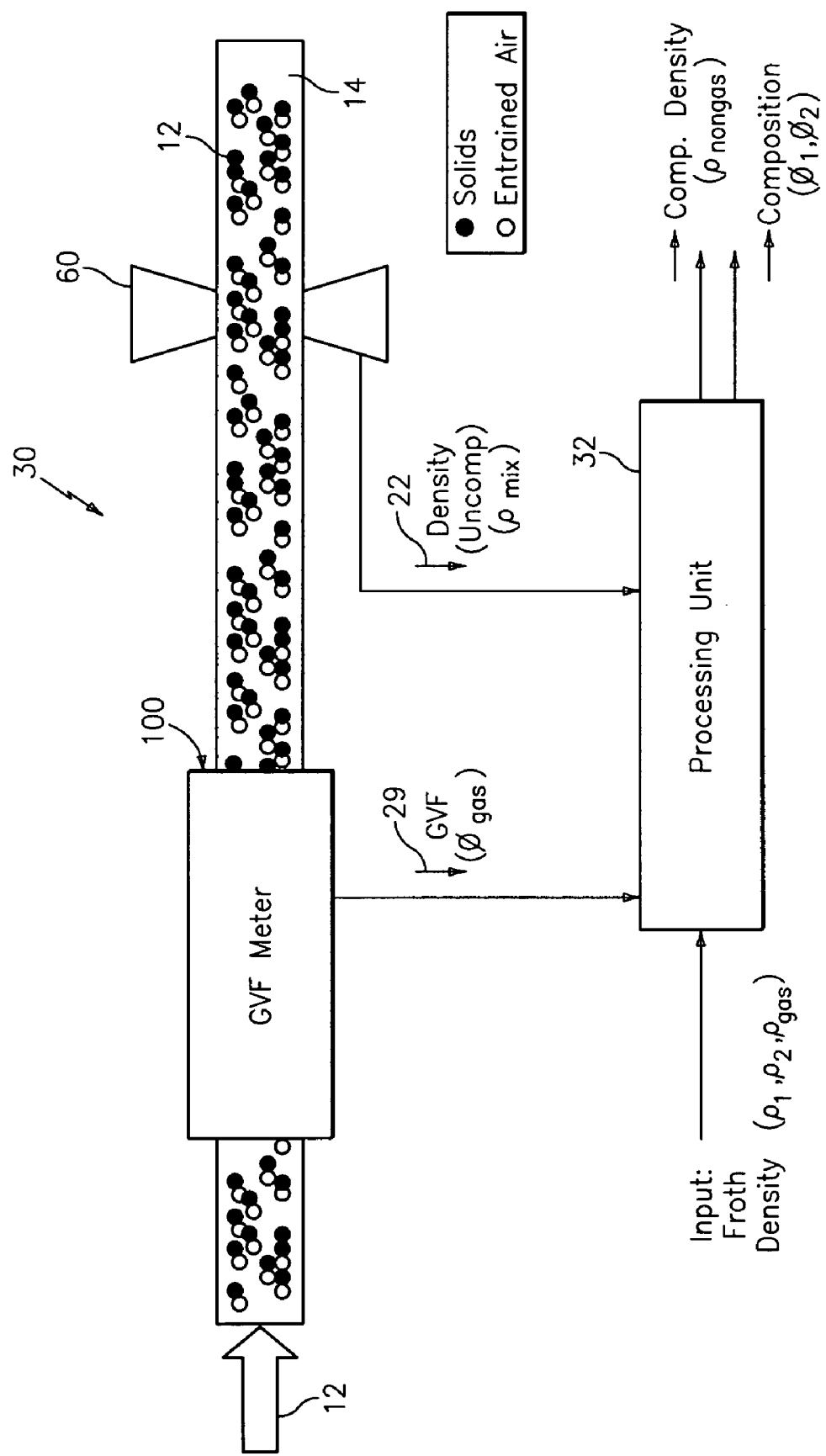
FIG. 4 is a schematic illustration of a flow measuring system for providing a density and/or composition measurement provided by a gamma densitometer augmented for entrained gas within a bitumen froth flow passing within a pipe, in accordance with the present invention.

Referring to FIG. 4, one example of an application for the flow measuring system 30 is in the oil sands industry, where monitoring entrained sand levels in bitumen/water froths is an important application. However, due to the presence of unknown amount of entrained air in the froth, an accurate measurement of the amount of particles (e.g., sand) is not possible using a gamma densitometer 60 operating on a bitumen froth mixture 12, which contains a small amount of entrained air and sand particles entrained in a liquid continuous mixture of bitumen and water. The density of bitumen and water ($\rho_1$) are nearly identical for most applications, therefore, variations in the bitumen/water cut of liquid phase has very limited effect on the mixture density. Variations in the mixture density are therefore due to the air and particles. The density of the particles ($\rho_2$) and the density of the air ($\rho_{gas}$) are known. By measuring the gas volume fraction of the entrained air ($\emptyset_{gas}$) and density of the fluid flow ($\rho_{mix}$) directly and knowing the density of the particles ($\rho_2$) and the density of the bitumen and water ($\rho_1$), the gamma densitometer 60 in combination with the entrained gas meter 100 provides a means to determine the amount of sand left ($\emptyset_2$) in the slurry as well as other parameters of the mixture, as described hereinbefore.

Figure 5:
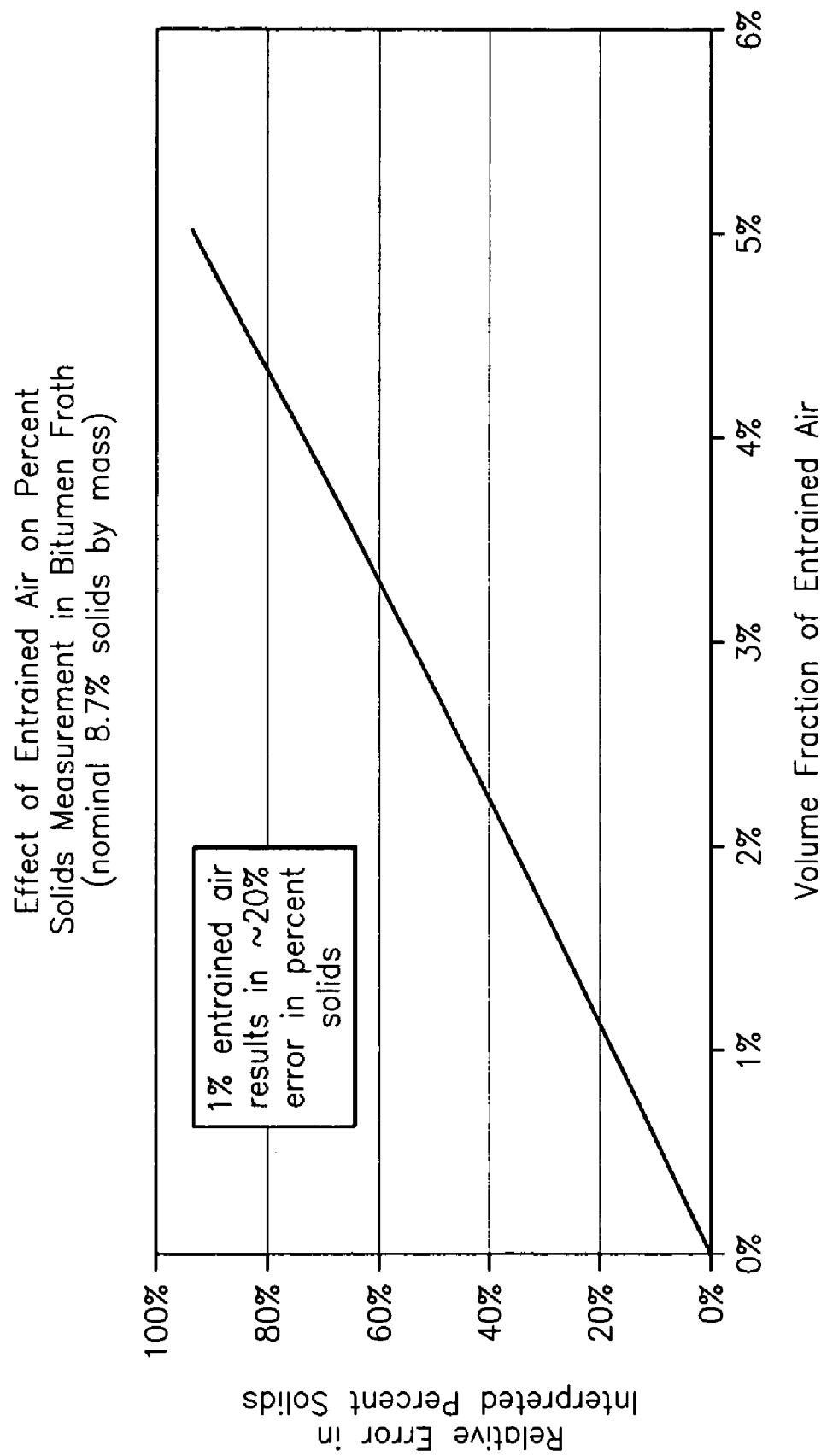
FIG. 5 is a plot of the relative error in the interpreted percent solids versus the gas volume fraction in a bitumen froth flow, in accordance with the present invention.

FIG. 5 is a plot of the relative error in interpreted percent of solids in a bitumen froth flow versus the gas fraction of entrained air/gas in the flow 12. As shown, a bitumen froth flow having 1% of entrained air therein results in an approximately 20% error in percent solids (e.g., sand) in the bitumen froth flow.

Figure 6:
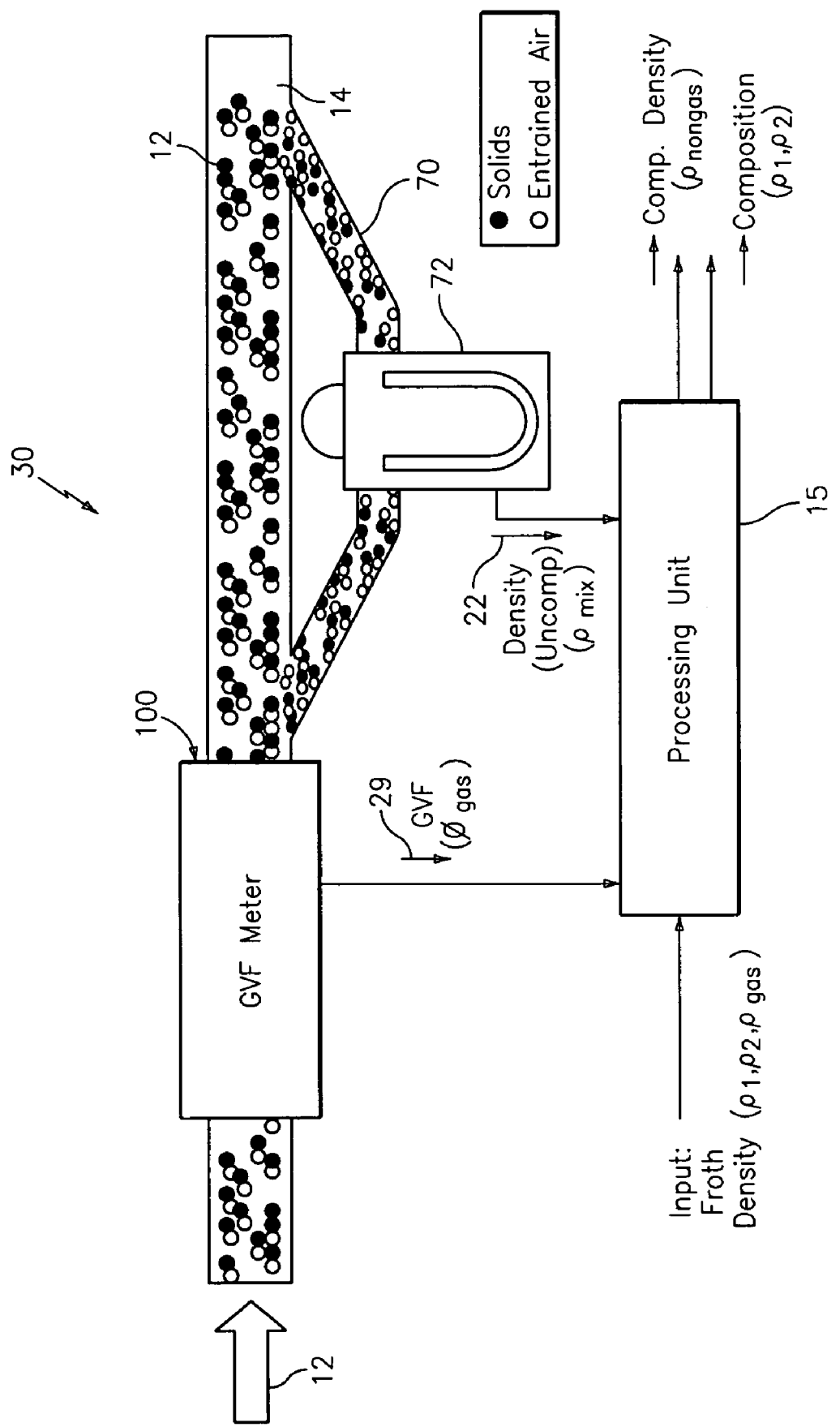
FIG. 6 is a schematic illustration of a flow measuring system for providing a density and/or composition measurement provided by a coriolis meter augmented for entrained gas within a bitumen froth flow passing within a pipe, in accordance with the present invention.

As shown in FIG. 4, the density measurement ($\rho_{nongas}$) and composition measurement ($\emptyset_1$, $\emptyset_2$) described above can be done on the full pipe, or as shown in FIG. 6, on a slip stream pipe 70. Referring to FIG. 6, a slip stream pipe 70 enables the use of a coriolis meter 72 to measure the density ($\rho_{mix}$) by providing a smaller diameter pipe. A further benefit of a sonar-based entrained air measurement is achieved when the sound speed measurement is used to enhance the accuracy of the coriolis on the aerated mixture, similar to that described in U.S. patent application Ser. No. 10/892,886, filed on Jul. 15, 2004, which is incorporated herein by reference. While the entrained gas meter 100 is shown mounted on the full pipe in FIG. 6, the present invention contemplates that the entrained air meter may be mounted on the slip stream pipe 70.

As shown in FIGS. 4 and 6, the apparatus 100 for measuring the gas volume fraction of the flow 12 may also provide a velocity measurement and a volumetric flow rate measurement of the flow, similar to that described in U.S. patent application Ser. No. 10/712,818, filed on Nov. 12, 2003, U.S. patent application Ser. No. 10/712,833, filed on Nov. 12, 2003, U.S. patent application Ser. No. 10/766,440, filed on Jan. 27, 2004, and U.S. patent application Ser. No. 10/875,857, filed on Jun. 24, 2004, which are incorporated herein by reference.

Coriolis meters provide a measurement of the mass flow and/or density of a fluid flow 12 passing through a pipe 14. A coriolis meter provides erroneous mass flow and density measurements in the presence of entrained gas within the fluid flow (e.g., bubbly gas). The present invention may also provide a means for compensating the coriolis meter to provide corrected or improved density and/or mass flow measurements.

While the gas volume fraction meter 100 may be used to determine the density of the non-gas component of the flow 12 and the composition of a multi-phase flow 12 as described hereinbefore, the GVF meter may be also used to compensate or augment the output density measurement and the mass flow measurement of a coriolis meter, similar to that described in U.S. patent application Ser. No. 10/892,886 filed Jul. 15, 2004, which is incorporated herein by reference.

In this embodiment, the coriolis meter 16 provides a frequency signal ($f_{nat}$) indicative of the natural frequency of the fluid 12 loaded tubes of the coriolis meter and the phase signal ($\Delta\phi$) indicative of the phase lag in the tubes of the coriolis meter. The GVF meter 100 or SOS measuring apparatus 18 provides an SOS signal 24 indicative of the speed of sound propagating through the fluid flow. A processing unit 32 processes the frequency signal, the phase signal and the SOS signal to provide at least one of the parameters of the fluid flow described hereinbefore, including the mass flow of the flow 12. Pressure and/or temperature signals may also be provided to the processing unit 32, which may be used to provide more accurate measurements of the gas volume fraction. The pressure and temperature may be measured by known means or estimated.

The coriolis meter may be any known coriolis meter, such as two inch bent tube coriolis meter manufactured my MicroMotion Inc. and a two in straight tube coriolic meter manufactured by Endress & Hauser Inc. The coriolis meters comprise a pair of bent tubes (e.g. U-shaped, pretzel shaped) or straight tubes as will be described hereinafter.

FIG. 7 illustrates a functional block diagram 80 of the flow measuring system of FIG. 2. As shown, the GVF meter 100 measures acoustic pressures propagating through the fluids to measure the speed of sound $\alpha_{mix}$. The GVF meter calculates at least gas volume fraction of the fluid and/or the reduced natural frequency using the measured speed of sound. The GVF meter may also use the pressure of the process flow to determine the gas volume fraction.

For determining an improved density for the coriolis meter, the calculated gas volume fraction and/or reduced frequency is provided to the processing unit 21. The improved density is determined using analytically derived or empirically derived density calibration models (or formulas derived therefore), which is a function of the measured natural frequency and at least one of the determined GVF, reduced frequency and speed of sound, or any combination thereof, which will be described in greater detail hereinafter. The improved density measurement is the density of the aerated flow passing through the pipe.

The present invention further contemplates determining improved compositional information of the aerated flow. In other words, knowing the speed of sound propagating through the flow and the improved density, the processing unit 21 can determine phase fraction of each component of the multiphase flow.

The present invention also contemplates compensating or improving the mass flow rate measurement of the coriolis meter 16, as shown in FIG. 7. For determining an improved mass flow rate for the coriolis meter, the calculated gas volume fraction and/or reduced frequency is provided to the processing unit 32. The improved mass flow rate is determined using analytically derived or empirically derived mass flow calibration models (or formulas derived therefore), which is a function of the measured phase difference ($\Delta\phi$) and at least one of the determined GVF, reduced frequency and speed of sound, or any combination thereof, which will be described in greater detail hereinafter. For determining an improved density for the coriolis meter, the calculated gas volume fraction and/or reduced frequency is provided to the processing unit 32. The improved density is determined using analytically derived or empirically derived density calibration/parameter models (or formulas derived therefore), which is a function of the measured natural frequency and at least one of the determined GVF, reduced frequency and speed of sound, or any combination thereof, which will be described in greater detail hereinafter. The improved mass flow measurement is the mass flow rate of the aerated flow passing through the pipe.

While the improved mass flow and improved density measurement may be a function GVF, SOS and reduced frequency, the present invention contemplates these improved measurements may be a function of other parameters, such a gas damping $\zeta_{gas}$.

Further, while the functional block diagram illustrates that the processing unit 32 may improve both the density measurement and the density measurement of the coriolis meter 16, the invention contemplates that the processing may only compensate or improve one the density and mass flow rate parameters.

Figure 8:
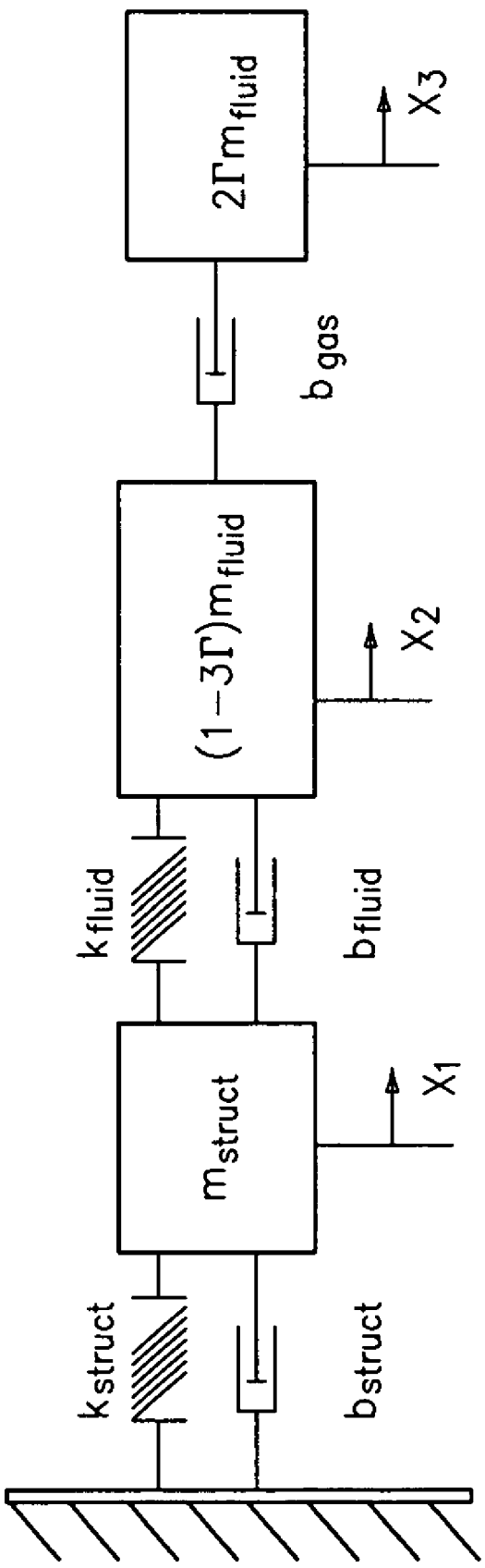
FIG. 8 is a schematic illustration of model of a coriolis meter having aerated fluid flowing therethrough that accounts for compressibility and inhomogeniety of the aerated fluid, in accordance with the present invention.

Results for a lumped parameter model of FIG. 8 presented hereinafter confirm long recognized accuracy degradation of vibrating tube density meters attributed to aeration. The models can be used to illustrate qualitatively the role of several non-dimensional parameters that govern the performance of the meters in aerated fluids. It can be concluded from these models that gas volume fraction plays a dominant role, with several other parameters including gas damping $\zeta_{gas}$ and reduced frequency also influencing performance.

The present invention provides an approach in which a speed-of-sound measurement of the process fluid is integrated with the natural frequency measurement of a vibrating tube density meter to form a system with an enhanced ability to operate accurately in aerated fluids. Introducing a real time, speed-of-sound measurement address the effects of aeration on multiple levels with the intent to enable vibrating-tube-based density measurement to continue to report liquid density in the presence of entrained air with accuracy approaching that for a non-aerated liquid. Firstly, by measuring the process sound speed with process pressure, the aeration level of the process fluid can be determined with high accuracy on a real time basis. Secondly, the real time measurements of sound speed, and the derived measurement of gas volume fraction, are then utilized with empirically derived correction factors to improve the interpretation of the measured natural frequency of the vibrating tubes in terms of the density of the aerated fluid. Thirdly, the combined knowledge of aerated mixture density and aerated mixture sound speed, enable the determination of the non-aerated liquid component density, providing improved compositional information. Note liquids phase includes pure liquids, mixtures of liquids, as well as liquid/solid mixtures.

To illustrate the fundamental ways in which aeration impacts vibrating-tube density measurements, a simplified, lumped parameter model for the effects of aeration in vibrating tubes is developed. The model illustrates that the effects of aeration can be attributed to at least two independent mechanisms; 1) the density inhomogeniety of discrete gas bubbles and 2) increased mixture compressibility due to aeration.

This basic framework provides an accurate means to determine process fluid density under most operating conditions. However, some of the fundamental assumptions regarding the interaction of the fluid 12 and the structure can deteriorate under different operating conditions. Specifically, aerated fluids in oscillating tubes behave differently from single phase fluids in two important ways; increased compressibility, and fluid inhomogeneity.

Fluid Compressibility

It is well known that most aerated liquids are significantly more compressible than non-aerated liquids. Compressibility of a fluid is directly related to the speed of sound and density of the fluid 12.

Mixture density and sound speed can be related to component densities and sound speed through the following mixing rules which are applicable to single phase and well-dispersed mixtures and form the basis for speed-of-sound-based entrained air measurement.

$$\kappa_{mix} = \frac{1}{\rho_{mix} a_{mix\infty}^2} = \sum_{i=1}^{N} \frac{\phi_i}{\rho_i a_i^2}$$

where $$\rho_{mix} = \sum_{i=1}^{N} \rho_i \phi_i$$

and $\kappa_{mix}$ is the mixture compressibility, and $\phi_i$ is the component volumetric phase fraction.

Consistent with the above relations, introducing air into water dramatically increases the compressibility of the mixture 12. For instance, at ambient pressure, air is approximately 25,000 times more compressible than water. Thus, adding 1% entrained air increases the compressibility of the mixture by a factor of 250. Conceptually, this increase in compressibility introduces dynamic effects that cause the dynamic of behavior of the aerated mixture within the oscillating tube to differ from that of the essentially incompressible single-phase fluid.

The effect of compressibility of the fluid 12 can be incorporated into a lumped parameter model of a vibrating tube as shown schematically in FIG. 8. The stiffness of the spring represents the compressibility of the fluid. As the compressibility approaches zero, the spring stiffness approaches infinity.

As before the effective mass of the fluid 12 is proportional to the density of the fluid and the geometry of the flow tube. The natural frequency of the first transverse acoustic mode in a circular duct can be used to estimate an appropriate spring constant for the model $$f = \frac{1.84}{\pi D} a_{mix} = \frac{1}{2\pi} \sqrt{\frac{K_{fluid}}{m_{fluid}}}$$

Note that this frequency corresponds to a wavelength of an acoustic oscillation of approximately two diameters, i.e., this transverse mode is closely related to a "half wavelength" acoustic resonance of the tube. For low levels of entrained air, the frequency of the first transverse acoustic mode is quite high compared to the typical structural resonant frequencies of coriolis meters of 100 Hz, however, the resonant acoustic frequency decreases rapidly with increased levels of entrained air.

In characterizing aeroelastic systems, it is often convenient to define a reduced frequency parameter to gauge the significance of the interaction between coupled dynamic systems. For a vibrating tube filled with fluid, a reduced frequency can be defined as a ratio of the natural frequency of the structural system to that of the fluid dynamic system.

$$f_{red} = \frac{f_{struct} D}{a_{mix}}$$

Where $f_{struct}$ is the natural frequency of the tubes in vacuum, D is the diameter of the tubes, and $a_{mix}$ is the sound speed of the process fluid. For this application, as the reduced frequency becomes negligible compared to 1, the system approaches quasi-steady operation. In these cases, models, which neglect the compressibility of the fluid is likely to be suitable. However, the effects of unsteadiness increase with increasing reduced frequency. For a given coriolis meter, mixture sound speed has the dominant influence of changes in reduced frequency. When considering coriolis meters of varying design parameters, increases in tube natural frequency or tube diameter will increase the effects of unsteadiness for a given level of aeration.

Fluid Inhomogeneity

In additional to dramatically increasing the compressibility of the fluid 12, aeration introduces inhomogeneity to the fluid. For flow regimes in which the gas is entrained in a liquid-continuous flow field, the first-order effects of the aeration can be modeled using bubble theory. By considering the motion of an incompressible sphere of density of $\rho_0$ contained in an inviscid, incompressible fluid with a density of $\rho$ and set into motion by the fluid show that the velocity of the sphere is given by:

$$V_{sphere} = \frac{3\rho}{\rho + 2\rho_0} V_{fluid}$$

For most entrained gases in liquids, the density of the sphere is orders of magnitude below that of the liquid and the velocity of bubble approaches three times that of the fluid.

Considering this result in the context of the motion of a sphere in a cross section of a vibrating tube, the increased motion of the sphere compared to the remaining fluid must result in a portion of the remaining fluid having a reduced level of participation in oscillation, resulting in a reduced, apparent system inertia.

In a lumped parameter model, a gas bubble of volume fraction $\phi$ is connected across a fulcrum 42 to a compensating mass of fluid with volume $2\Gamma$, where $\Gamma$ is the gas volume fraction of the flow. The fulcrum is rigidly connected to the outer pipe 14. The effects of viscosity can be modeled using a damper connected to restrict the motion of the gas bubble with respect to the rest of the liquid and the tube itself. The remaining volume of liquid in the tube cross section $(1-3\Gamma)$ is filled with an inviscid fluid. In the inviscid limit, the compensating mass of fluid $(2\Gamma)$ does not participate in the oscillations, and the velocity of the mass-less gas bubble becomes three times the velocity of the tube. The effect of this relative motion is to reduce the effective inertia of the fluid inside the tube to $(1-3\Gamma$ times that presented by a homogeneous fluid-filled the tube. In the limit of high viscosity, the increased damping constant minimizes the relative motion between the gas bubble and the liquid, and the effective inertia of the aerated fluid approaches $1-\Gamma$. The effective inertia predicted by this model of an aerated, but incompressible, fluid oscillating within a tube agrees with those presented by (Hemp, et al, 2003) in the limits of high and low viscosities.

One should appreciate that the processing unit may use these models independently or together in a lumped parameter model.

Combined Lumped Parameter Model

Models were presented with the effects of aeration on vibrating tube density meters in which the effects of compressibility and inhomogeniety were addressed independently. FIG. 8 shows a schematic of a lumped parameter model that incorporates the effects of compressibility and inhomogeniety using the mechanism-specific models developed above.

The equations of motion of the above lumped parameter model, assuming solutions in the form of $e^{st}$ where s is the complex frequency, can be expressed in non-dimensional form as:

$$\begin{bmatrix} s+2\alpha\zeta_f Q+2\zeta_s & 1+\alpha Q^2 & -2\alpha\zeta_f Q & -\alpha Q^2 & 0 & 0 \\ -1 & s & 0 & 0 & 0 & 0 \\ 2\zeta_f Q & -Q^2 & (1-3\Gamma)s+2\zeta_f Q+2\zeta_g & Q^2 & -2\zeta_g & 0 \\ 0 & 0 & -1 & s & 0 & 0 \\ 0 & 0 & -2\zeta_g & 0 & 2\Gamma s+2\zeta_g & 0 \\ 0 & 0 & 0 & 0 & -1 & s \end{bmatrix} \begin{Bmatrix} y_1 \\ x_1 \\ y_2 \\ x_2 \\ y_3 \\ x_3 \end{Bmatrix} = 0$$

The parameters governing the dynamic response of the model are defined in the following Table 1.

TABLE 1

Definition of Non-dimensional Parameters Governing the Equation of Motion for the Lumped Parameter Model of a Tube Filled with a Compressible, Aerated Fluid

| Symbol | Description | Definition |
| --- | --- | --- |
| $\alpha$ | Mass ratio | $m_{fluid}/m_{struct}$ |
| Q | Natural Frequency Ratio | $\omega_{fluid}/\omega_{struct}$ |
| $\zeta_f$ | Critical Damping Ratio of Fluid System | $b_{fluid}/(2m_{fluid}\omega_{fluid})$ |
| $\zeta_s$ | Critical Damping Ratio of Structural System | $b_{struc}/(2m_{struct}\omega_{sstruc})$ |
| $\zeta_g$ | Critical Damping Ratio of Structural System | $b_{gas}/(2m_{fluid}\omega_{struct})$ |
| $\tau$ | Non-dimensional time | $t\,\omega_{struct}$ |
| y | Non-dimensional temporal derivative of x | $dx/d\tau$ |

Solving the sixth-order eigenvalue problem described above provides a means to assess the influence of the various parameters on the observed density. The natural frequency of the primary tube mode predicted by the eigenvalue analysis is input into the frequency/density from the quasi-steady, homogeneous model to determine the apparent density of the fluid 12 as follows.

$$\rho_{apparent} = \frac{\rho_{liq}}{\alpha}\left(\frac{f_s^2}{f_{observed}^2} - 1\right)$$

As a baseline condition, a "representative" coriolis meter with parameters given in Table 2 was analyzed.

TABLE 2

Parameters Defining the Baseline Vibrating Tube Density Meter

| Parameter | Description | Value |
| --- | --- | --- |
| $f_s$ | Structural Frequency of Tubes | 100 Hz |
| $\alpha$ | Mass ratio | 1.25 |
| $\zeta_{struct}$ | Critical Damping Ratio - structure | 0.01 |
| $\zeta_{fluid}$ | Critical Damping Ratio - fluid | 0.01 |
| $\zeta_{gas}$ | Critical Damping Ratio - gas | 0.01 |
| Q | Frequency Ratio | As determined by sound speed of air/water at STP and structural parameters |
| D | Tube diameter | 1.0 inches |

For a given coriolis meter, the level of aeration has a dominant effect on the difference between actual and apparent mixture density. However, other parameters identified by the lumped parameter model also play important roles. For example, the damping parameter associated with the movement of the gas bubble relative to the fluid within the tube, $\zeta_{gas}$, is a parameter governing the response of the system to aeration. For $\zeta_{gas}$ approaching zero, the apparent density approaches $1-3\Gamma$, i.e., the meter under reports the density of the aerated mixture by $2\Gamma$. However, as the $\zeta_{gas}$ is increased, the apparent density approaches the actual fluid density of $1-\Gamma$.

The influence of compressibility is function of gas volume fraction for a range of meters differing only in natural frequency of the tubes. The natural frequency of the tubes, primarily through the influence of the reduced frequency of operation at a given level of aeration can significantly influence the relation between the actual and apparent density of an aerated fluid.

Mass Flow Correction

The current state-of-the-art appears to utilize quasi-steady models, and empirical correlations based on quasi-steady models, to relate the measured quantities to the derived fluid parameters. This quasi-steady model for the fluid structure interactions appears to work adequately for most Coriolis meters operating with most industrial process flows. The validity of the quasi-steady assumption will scale with the reduced frequencies of the vibration of the fluid within the pipe. Under a quasi-steady framework, the higher the reduced frequencies, the less accurate the Coriolis meters become.

One relevant reduced frequency for the unsteady effects within a Corilois meter is the reduced frequency based on the vibrational frequency, tube diameter, and process fluid sound speed:

$$\tilde{f}_D = \frac{fD}{a_{mix}}$$

Another relevant reduced frequency is the that based on the overall length of the corilois tubes:

$$\tilde{f}_L = \frac{fL}{a_{mix}}$$

It should be noted that, for any given meter design in which the geometry is fixed, the two reduced frequencies are not independent, and are scalar multiples of each other. For a given meter, variations in the reduced frequencies above are primarily determined by variations in process fluid sound speed.

Physically, the reduced frequency represents the ratio between the time required for sound to propagate over a characteristic length to the time required for the tube to vibrate one cycle. From a performance and accuracy perspective, reduced frequencies serve to capture the importance of unsteadiness in the aeroelastic interaction of the fluid and structure.

In the limit of reduced frequencies approaching zero, the process can be modelled as quasi-steady. Most analytical models of Corilois flow meters use a quasi-steady model for the fluid/structure interaction. However, for non-zero reduced frequencies, unsteady effects begin to influence the relationship between the measured structural response, i.e. the phase lag in the two legs of the meters and the natural frequency, and the sought fluid parameters, i.e. the mass flow of the fluid and fluid density.

However, what is disclosed herein is to use a sound-speed based gas volume fraction parameter, a reduced frequency parameter relating to phase lag to mass flow rate.

If the reduced frequency based on diameter is non-negligible, the inertial load from the fluid on the pipe develops a slight phase lags that increases with increasing frequency. For non-negligible reduced frequencies based on the length of the flow tube, oscillations in the flow velocity can vary over the length of the pipe, potentially introducing error in the output of the meter. Typical variations in mixture sound speeds due to two phase flow result in significant variations in reduced frequencies.

Thus, by dramatically reducing mixture speed of sound, the introduction of gas to a liquid mixture can dramatically increase the reduced frequency of the primary vibration associated with the Coriolis meter. If not accounted for in the interpretation, this increase in reduced frequency renders the quasi-steady model increasing inaccurate, and results in errors in mass flow and in density.

This decrease in accuracy of Corilois meters with the introduction of bubbly fluids is well documented. In fact, others have attempted to correct for the effect of entrained air by correlating observed errors in mass flow to the gas volume fraction within the process fluid. These authors proposed a correction based on GVF as follows:

$$R = \frac{2\alpha}{1-\alpha}$$

Where the α represents the gas volume fraction and R represents decrease in measured (apparent) mass flow normalized by the true mass flow. Thus, using this correlation, a 1% increase in entrained air would result in a roughly 2% underestimate of the actual mass flow.

Although this formulation appears to capture the general trend observed experimentally, it has two drawbacks for use in the field. Firstly, the coriolis meter 16 has no direct way to measure the gas volume fraction. It has been suggested to use the measured apparent density of the fluid to estimate the level of entrained air, however, this is problematic since both of the two fundamental measurements, phase difference and natural frequency, are impacted by changes in the reduced frequency of the Coriolis vibration. Secondly, it is unlikely that the gas volume fraction is the only variable influencing the relationship between measured phase difference and mass flow and the measured natural frequency and density. Although gas volume fraction appears to correlate over at least some range of parameters, the physics of the problem suggest that sound speed, via a reduced frequency effect, may have also direct influence on the interpretation as developed above.

What is proposed in this disclosure is to use a direct sound measurement from the process fluid to aid in the interpretation of the coriolis meter 16. In this interpretation, the reduced frequency parameters developed herein is included in interpreting the relation between the phase difference in the vibrating tubes and the mass flow as well as a direct role in interpreting the natural frequency of the oscillating flow tubes in terms of process fluid density. The sound speed measurement, combined with knowledge of process liquid and gas components as well as process temperature and pressure, enables a direct measurement of entrained air as well. Thus, the reduced frequency parameter and gas volume fraction can be used as inputs in the interpretation of phase lag in terms of mass flow.

Due to the strong relationship between air content in liquids and mixture sound speed, the role of the reduced frequency parameter in the interpretation of the fundamental measurement of the Coriolis meter will have a more pronounce effect in bubbly flows. However, changes in sound speed and hence reduced frequency of operation in various types of liquids and other process mixtures have an effect on the interpretation and hence accuracy of Coriolis meter used in these applications as well. Consider, flow example, the performance of a Coriolis meter on two liquids—water and oil. Assume that the fluids have different densities and sound speeds. The different fluid properties suggest that the Coriolis meters will be operating at different reduced frequencies. The reduced frequency for the water will typically be ~10%–30% lower than that for the oil application.

Recognizing that, while they are different, the reduced frequencies for both applications are still "small", the impact on accuracy may not be significant. However, some degree of inaccuracy is introduced by not accounting for the differences in the reduced frequency of operation of the Coriolis meter in this application.

In this facility, water is pumped from the bottom of a large separator through a mag meter which measures the volumetric flow rate of the water. The water then flows through a SONARtrac entrained air meter to verify that the water has negligible entrained air. Air is then injected into the water forming a two phase mixture. The amount of entrained air is then measured with a second SONARtrac meter. The two phase mixture, of known water and air composition then passes through a 3 inch, bent tube Corilois meter. The outputs of all of the above mentioned metering devices where recorded along with water pressure and temperature. Using this information, the errors associated with the coriolis meter operating in the aerated liquids can be determined and plotted as a function of sound speed based parameters. In this example, Coriolis meter performance is characterized as a function of gas volume fraction. The errors were indeed significant. At 2% entrained air, the Coriolis meter is over reporting mass flow by 15% and under reporting mixture density by 2%. The actual density being reported by the meter, if interpreted as the density of the liquid phase in the meter would be roughly 4% in error.

For this example, the mass flow error is parameterized by the sound speed-based gas volume fraction of entrained air. The parametric dependence of this is given by the equation shown on the plot.

Mass Factor=$0.0147gvf^3 - 0.0018gvf^2 + 0.0041gvf + 1.0009$

This correlation was then used to correct for the coriolis mass flow for the presence of entrained air. The amount of entrained air injected upstream of the Coriolis meter was varied in small increments such that the total entrained air levels ranged from 0 to 2%. The Coriolis meter registers and significant errors in mass flow (up to 15%) due to entrained air and the gas volume fraction based correlation employed successfully corrects the mass flow errors to within roughly 1% for the demonstration.

A flow measuring system 82 embodying the present invention may be used monitor well heads. A basic configuration of a well metering system 84 is shown schematically in FIG. 9. This approach addresses most well head flow conditions and utilizes a two phase separator 86 (e.g., gas/liquid cylindrical cyclone (GLCC) separator) to separate the production stream of a gas/oil/water mixture 12 into a mostly gas stream 88 and a mostly liquid stream 89. While a GLCC is provide in the metering system 84, the present invention contemplates any device that separates the air and liquid components.

The mostly gas stream 88 is fed to a sonar-based flow meter 89 similar as flow meter 90 which will be described in greater detail herein after. The flow meter measures the flow rate of the gas and determines the gas volume fraction of the gas fluid.

The mostly liquid stream 89 is fed into a sonar-based flow meter 90, similar to the meters 18 and 100 of FIGS. 1 and 2 respectively, which measures mixture sound speed and possibly convective velocity to determine the gas volume fraction and the volumetric flow rate, respectively, of the liquid/gas mixture 89. The flow meter 90 is similar to that described in U.S. patent application Ser. No. 10/875,857 filed Jun. 24, 2004, U.S. patent application Ser. No. 10/766,440 and U.S. patent application Ser. No. 10/762,410, which are incorporated herein by reference. Following the flow meter 90, the flow 89 enters a coriolis meter 16. A processing unit 92 receives the output signals from the flow meter 90 and coriolis meter 16 to provide the measured outputs shown in FIGS. 3 and 8.

The two processing options for measuring the aerated liquid mass flow and density are presented in FIG. 7. The first method assumes that the performance of the coriolis for both mass flow and density can be augmented using the methods described in U.S. patent application Ser. No. 10/892,886 and U.S. Provisional Patent Application No. 60/539,640, which are incorporated herein by reference. The second approach, described in FIG. 11, assumes that only the density measurement of the coriolis meter is used for the mass flow and density of the aerated liquid. In this second approach, the volumetric flow rate determined by the flow meter 90 is combined with the corrected density to determine mass flow when aeration levels (e.g., gas volume fraction) exceed a threshold value. This approach takes advantage of the present inventions ability to determine a mass flow rate compensated for entrained gas and the corolis ability to accurately mass flow rate for flows 12 having low levels of aeration.

The second approach can be described as follows. To determine the density, the speed of sound (SOS) measurement provided by the flow meter 90 and the pressure (P) measurement provided by a pressure sensor 98 (or may be estimated) are used to calculate gas volume fraction and/or reduced frequency parameter of the coriolis meter operating on the aerated fluid. Next the mixture density is determined by correcting the output of the Coriolis-based density meter for the effects of aeration (as described in similar to that described in U.S. patent application Ser. No. 10/892,886. Direct measurement of the mixture density along with knowledge of the gas volume fraction and the gas density enables determination of liquid phase density, as described hereinbefore.

Mass flow is determined via one of two methods, depending on the gas volume fraction measurement of the flow meter 90. As shown in FIG. 11, if the gas volume fraction measurement is below a predetermined or input threshold level, the mass flow reported by the Coriolis is used. If it is above a threshold, the mass flow is calculated by first determining the total mixture volumetric flow rate by the flow meter 90 and then multiplying this value by corrected mixture density as described above.

Figure 10:
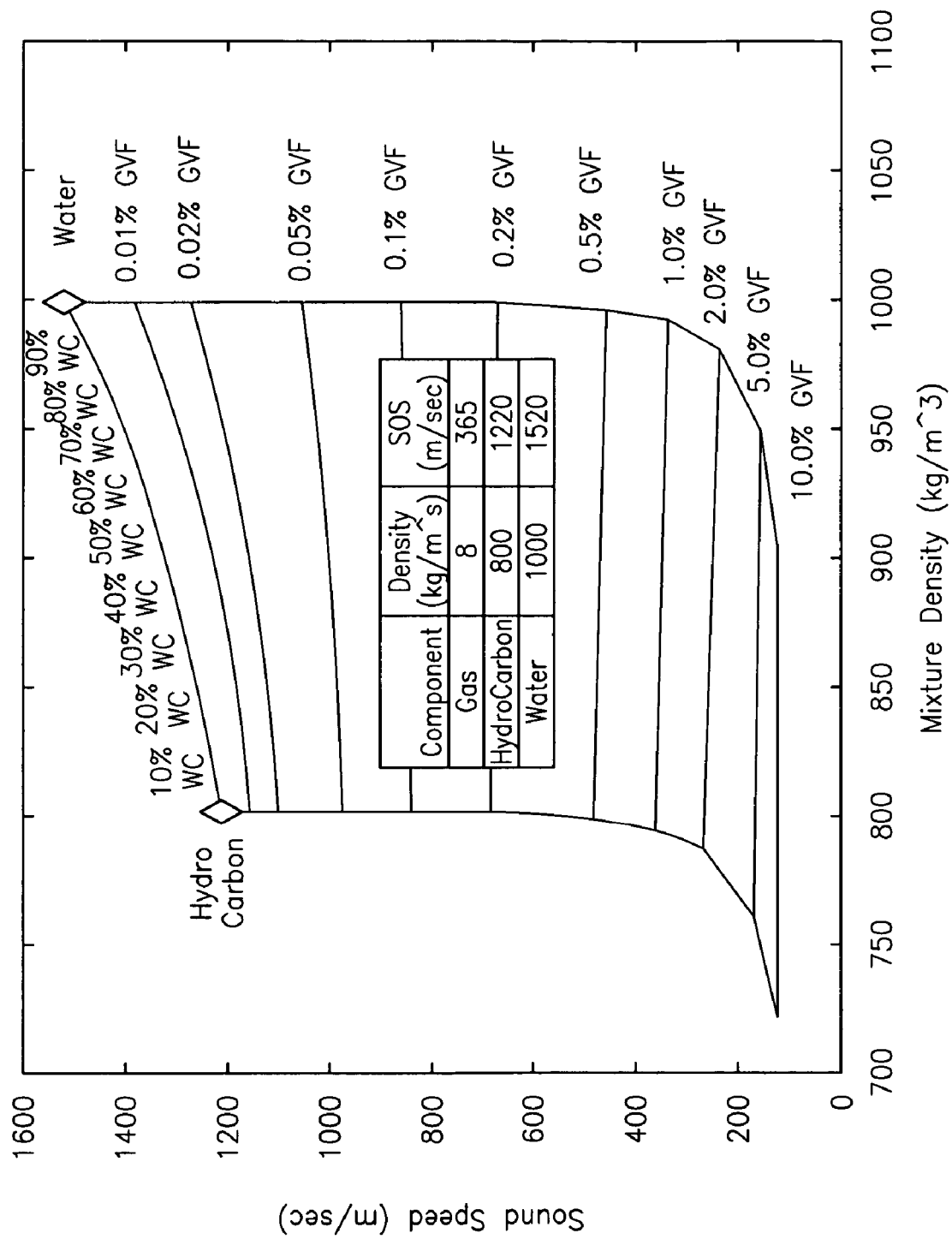
FIG. 10 is a plot of three phase composition of an aerated hydrocarbon and water fluid flow as a function of sound speed and flow density, in accordance with the present invention.

The combination of mixture sound speed and density enables a full description of the three phase fractions, i.e. the oil, water, and gas volumetric phase fraction, as described hereinbefore in accordance with present invention and shown in FIG. 10.

The mostly gas stream 88 is feed in a sonar-based flow meter 99 similar to that described hereinbefore and in U.S. patent application Ser. No. 10/875,857 filed Jun. 24, 2004, U.S. patent application Ser. No. 10/766,440 and U.S. patent application Ser. No. 10/762,410. The flow meter 99 measures sound speed and volumetric flow rate of the gas stream 88, and optionally an orifice plate may be used to measure the gas stream momentum. Combination of volumetric flow, sound speed and momentum measurements enables a good measurement of gas rate and liquid rate. The oil/water cut of the liquid phase of the mostly gas mixture can be assumed to be the same as the oil/water cut of the mostly liquid stream.

The result is a compact, versatile, economical three phase metering system.

Figure 9:
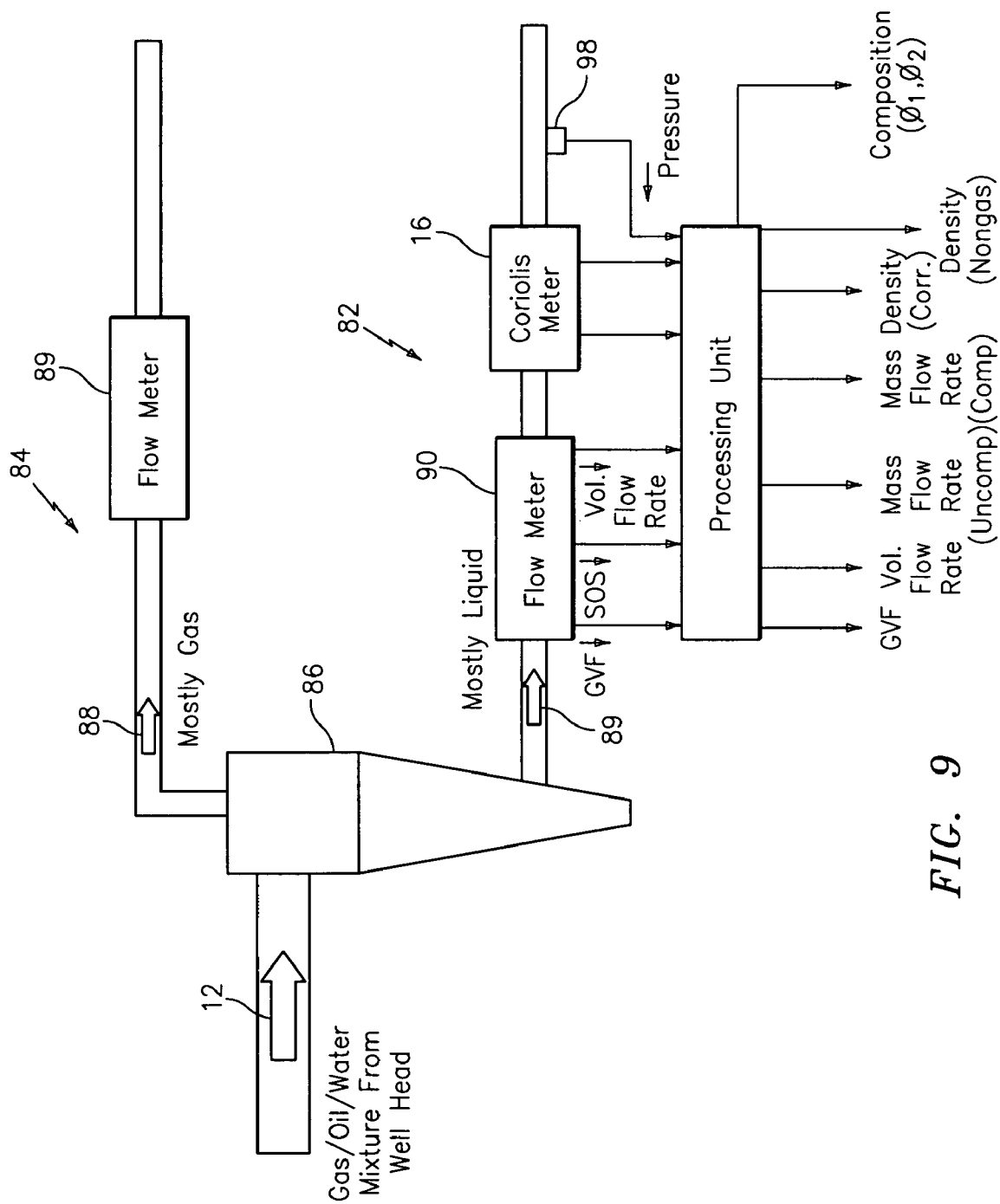
FIG. 9 is a schematic illustration of a well head monitoring system for providing a density and/or composition measurement provided by a coriolis meter augmented for entrained gas within a bitumen froth flow passing within a pipe, in accordance with the present invention.
Figure 12:
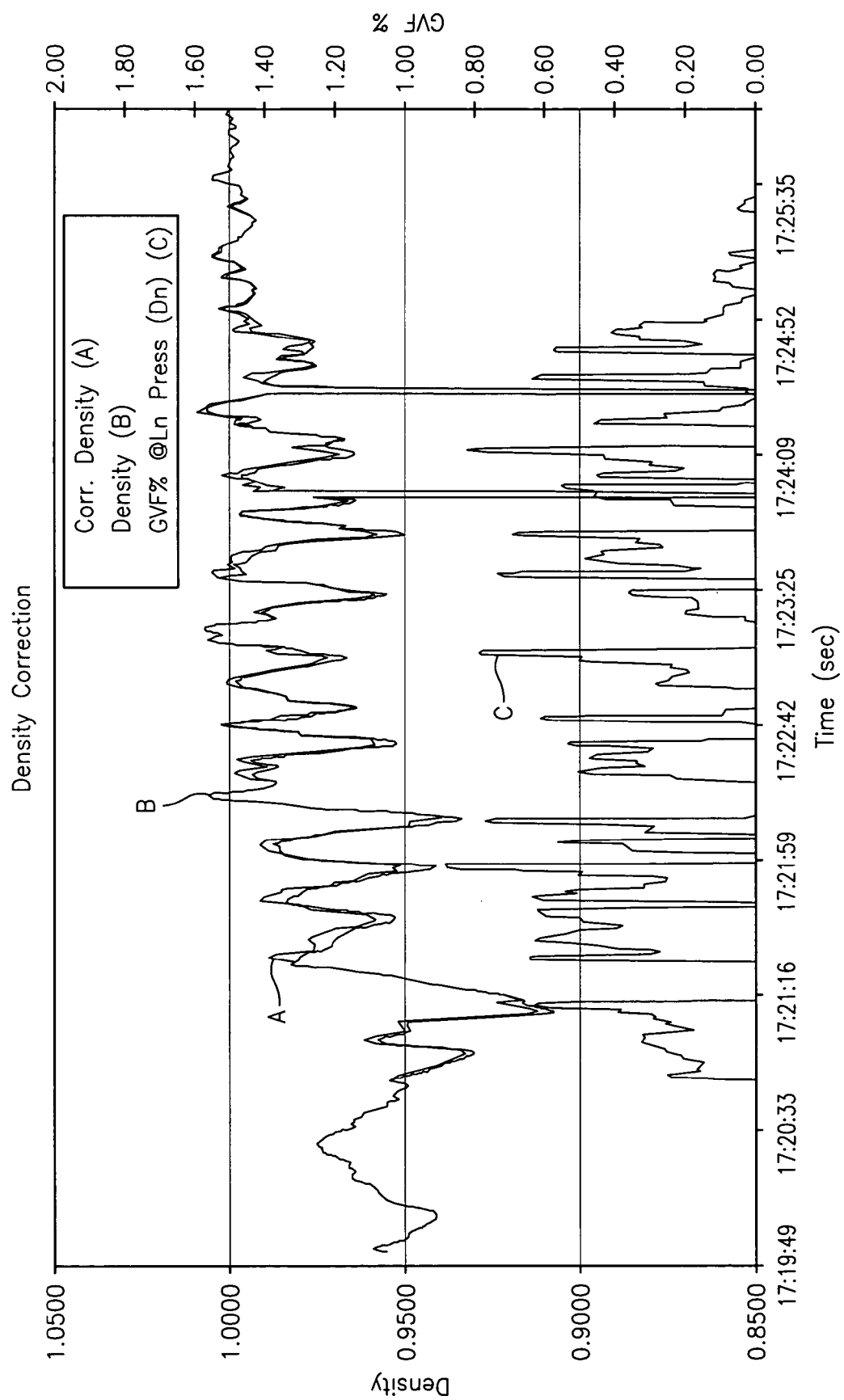
FIG. 12 is a plot the density correction and gas volume fraction of a fluid determined by a flow system embodying the present invention
Figure 13:
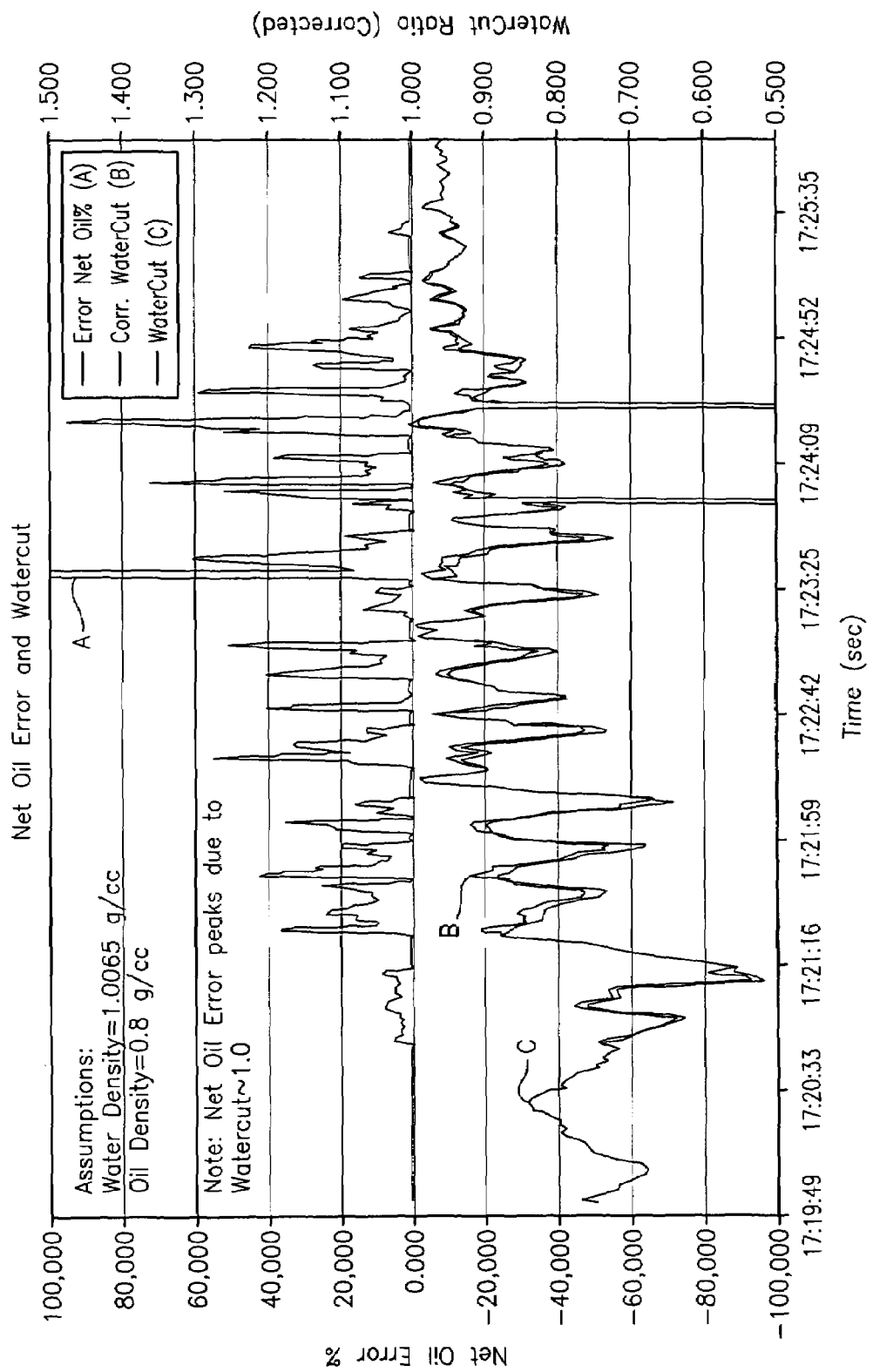
FIG. 13 is a plot of net oil error and watercut of three phase fluid flow determined by a flow system embodying the present invention.
Figure 14:
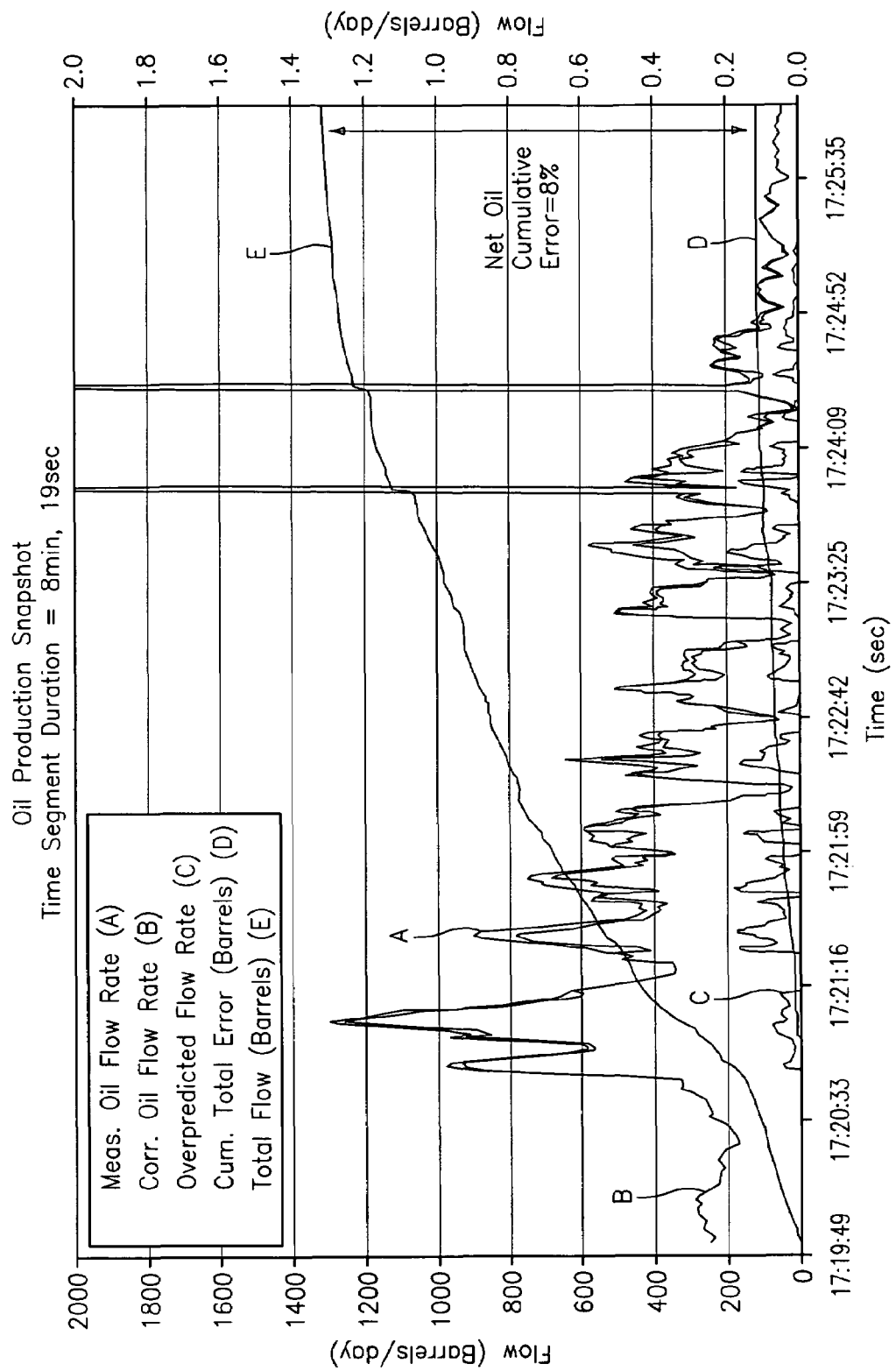
FIG. 14 is a plot of a snap shot of three phase fluid flow determined by a flow system embodying the present invention.

Tests were conducted on such a well metering system similar to that described in FIG. 9 to evaluate the performance of the flow meter 90 used in combination with the set-up shown in FIG. 9. FIGS. 12–14 illustrated data recorded from the coriolis meter 16 and the flow meter 90 to determine various parameters of the process fluid (e.g., oil/water/gas mixture). Specifically, FIG. 12 shows the density correction of the coriolis meter 16. FIG. 13 shows the net oil and water cut of the process fluid. FIG. 14 shows a snapshot of the oil production being pumped from ground.

As one will appreciate, the sonar-based entrained air meter 16 enables coriolis meters to maintain single phase accuracy in presence of entrained air.

Figure 15:
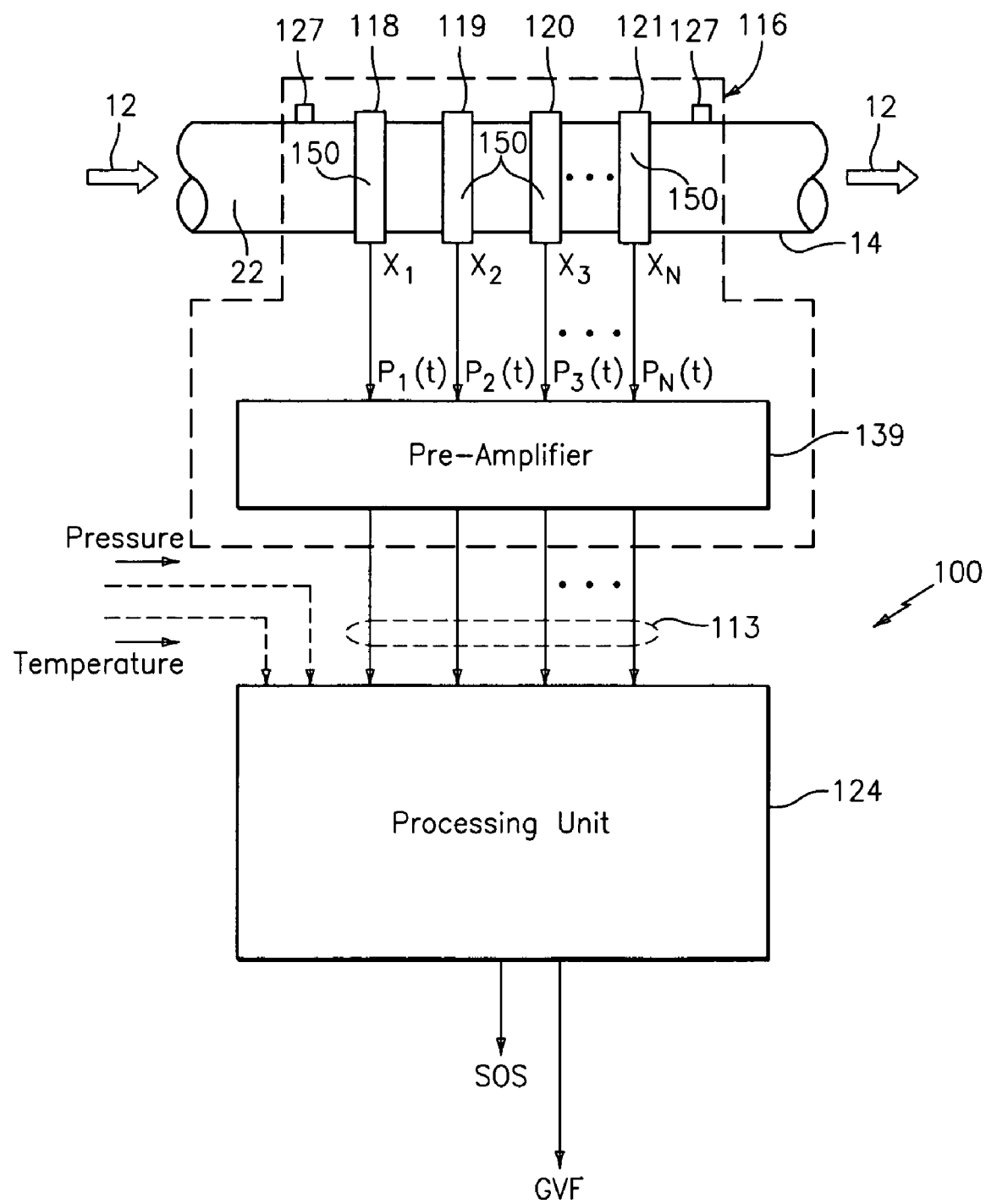
FIG. 15 is a schematic block diagram of a gas volume fraction meter, in accordance with the present invention.

FIG. 15 illustrates a gas volume fraction meter 100 of FIG. 2, as described herein before. The GVF meter 100 includes a sensing device 116 disposed on the pipe 14 and a processing unit 124. The sensing device 116 comprises an array of strain-based sensors or pressure sensors 118–121 for measuring the unsteady pressures produced by acoustic waves propagating through the flow 12 to determine the speed of sound (SOS). The pressure signals $P_1(t)$–$P_N(t)$ are provided to the processing unit 124, which digitizes the pressure signals and computes the SOS and GVF parameters. A cable 113 electronically connects the sensing device 116 to the processing unit 124. The analog pressure sensor signals $P_1(t)$–$P_N(t)$ are typically 4–20 mA current loop signals.

The array of pressure sensors 118–121 comprises an array of at least two pressure sensors 118, 119 spaced axially along the outer surface 122 of the pipe 14, having a process flow 112 propagating therein. The pressure sensors 118–121 may be clamped onto or generally removably mounted to the pipe by any releasable fastener, such as bolts, screws and clamps. Alternatively, the sensors may be permanently attached to, ported in or integral (e.g., embedded) with the pipe 14. The array of sensors of the sensing device 116 may include any number of pressure sensors 118–121 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the flow. Therefore, the number of sensors used is dependent at least on the degree of accuracy desired and the desire update rate of the output parameter provided by the apparatus 100. The pressure sensors 118–119 measure the unsteady pressures produced by acoustic waves propagating through the flow, which are indicative of the SOS propagating through the fluid flow 12 in the pipe. The output signals ($P_1(t)$–$P_N(t)$) of the pressure sensors 118–121 are provided to a pre-amplifier unit 139 that amplifies the signals generated by the pressure sensors 118–121. The processing unit 124 processes the pressure measurement data $P_1(t)$–$P_N(t)$ and determines the desired parameters and characteristics of the flow 12, as described hereinbefore.

The apparatus 100 also contemplates providing one or more acoustic sources 127 to enable the measurement of the speed of sound propagating through the flow for instances of acoustically quiet flow. The acoustic source may be a device the taps or vibrates on the wall of the pipe, for example. The acoustic sources may be disposed at the input end of output end of the array of sensors 118–121, or at both ends as shown. One should appreciate that in most instances the acoustics sources are not necessary and the apparatus passively detects the acoustic ridge provided in the flow 12, as will be described in greater detail hereinafter. The passive noise includes noise generated by pumps, valves, motors, and the turbulent mixture itself.

As suggested and further described in greater detail hereinafter, the apparatus 10 has the ability to measure the speed of sound (SOS) by measuring unsteady pressures created by acoustical disturbances propagating through the flow 12. Knowing or estimating the pressure and/or temperature of the flow and the speed of sound of the acoustic disturbances or waves, the processing unit 124 can determine gas volume fraction, such as that described in U.S. patent application Ser. No. 10/349,716, filed Jan. 23, 2003, U.S. patent application Ser. No. 10/376,427, filed Feb. 26, 2003, U.S. patent application Ser. No. 10/762,410, filed Jan. 21, 2004, which are all incorporated by reference.

Figure 16:
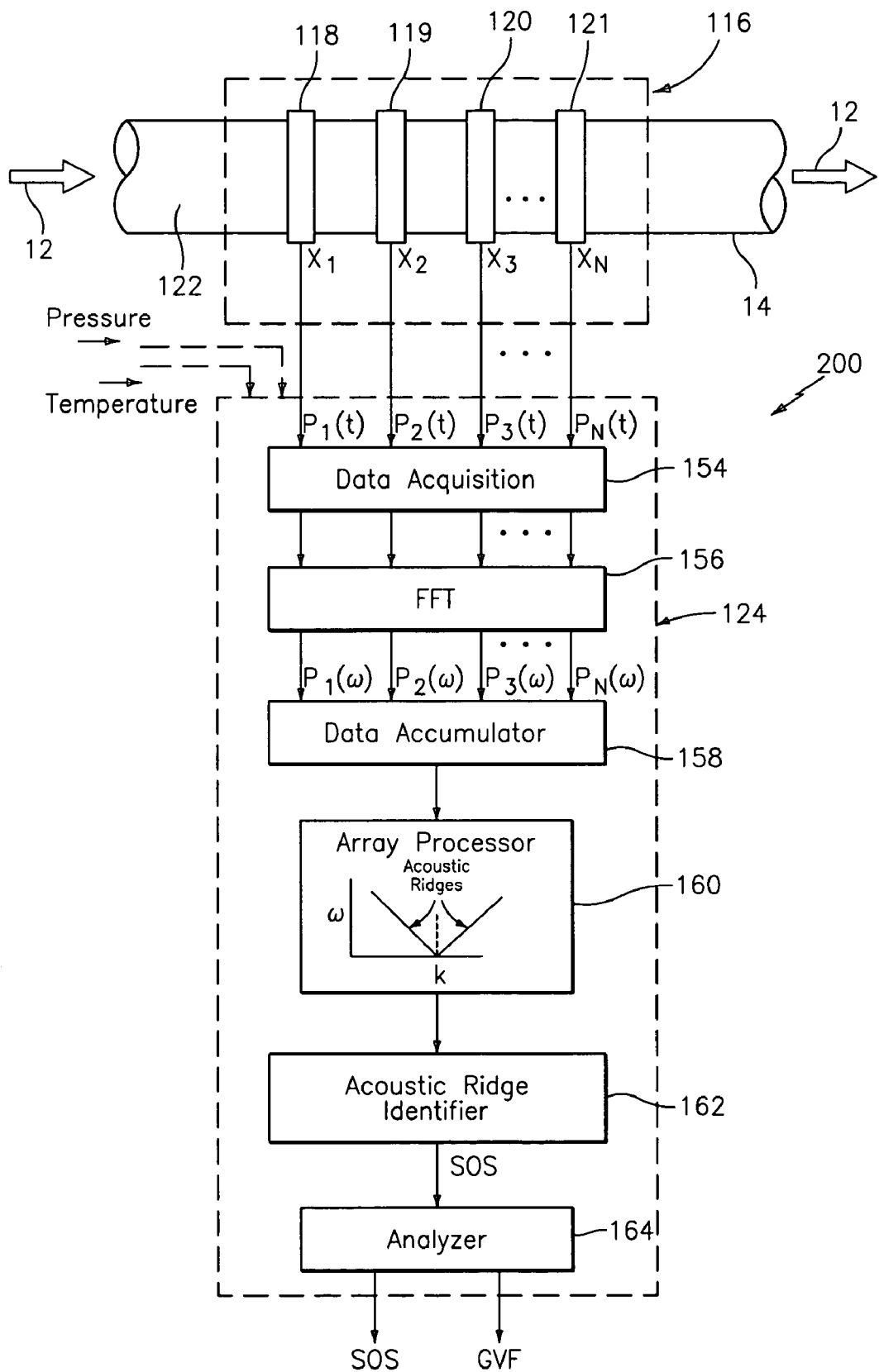
FIG. 16 is a schematic block diagram of another embodiment of gas volume fraction meter, in accordance with the present invention.

Similar to the apparatus 100 of FIG. 15, an apparatus 200 of FIG. 16 embodying the present invention has an array of at least two pressure sensors 118,119, located at two locations $x_1$, $x_2$ axially along the pipe 14 for sensing respective stochastic signals propagating between the sensors 118,119 within the pipe at their respective locations. Each sensor 118,119 provides a signal indicating an unsteady pressure at the location of each sensor, at each instant in a series of sampling instants. One will appreciate that the sensor array may include more than two pressure sensors as depicted by pressure sensor 120,121 at location $x_3$, $x_N$. The pressure generated by the acoustic pressure disturbances may be measured through strained-based sensors and/or pressure sensors 118–121. The pressure sensors 118–121 provide analog pressure time-varying signals $P_1(t), P_2(t), P_3(t), P_N(t)$ to the signal processing unit 124. The processing unit 124 processes the pressure signals to first provide output signals 151,155 indicative of the speed of sound propagating through the flow 12, and subsequently, provide a GVF measurement in response to pressure disturbances generated by acoustic waves propagating through the flow 12.

The processing unit 124 receives the pressure signals from the array of sensors 118–121. A data acquisition unit 154 digitizes pressure signals $P_1(t)$–$P_N(t)$ associated with the acoustic waves 14 propagating through the pipe 114. An FFT logic 156 calculates the Fourier transform of the digitized time-based input signals $P_1(t)$–$P_N(t)$ and provide complex frequency domain (or frequency based) signals $P_1(\omega), P_2(\omega), P_3(\omega), P_N(\omega)$ indicative of the frequency content of the input signals.

A data accumulator 158 accumulates the additional signals $P_1(t)$–$P_N(t)$ from the sensors, and provides the data accumulated over a sampling interval to an array processor 160, which performs a spatial-temporal (two-dimensional) transform of the sensor data, from the xt domain to the k-ω domain, and then calculates the power in the k-ω plane, as represented by a k-ω plot, similar to that provided by the convective array processor 146.

To calculate the power in the k-ω plane, as represented by a k-ω plot (see FIG. 17) of either the signals or the differenced signals, the array processor 160 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 118–121.

Figure 17:
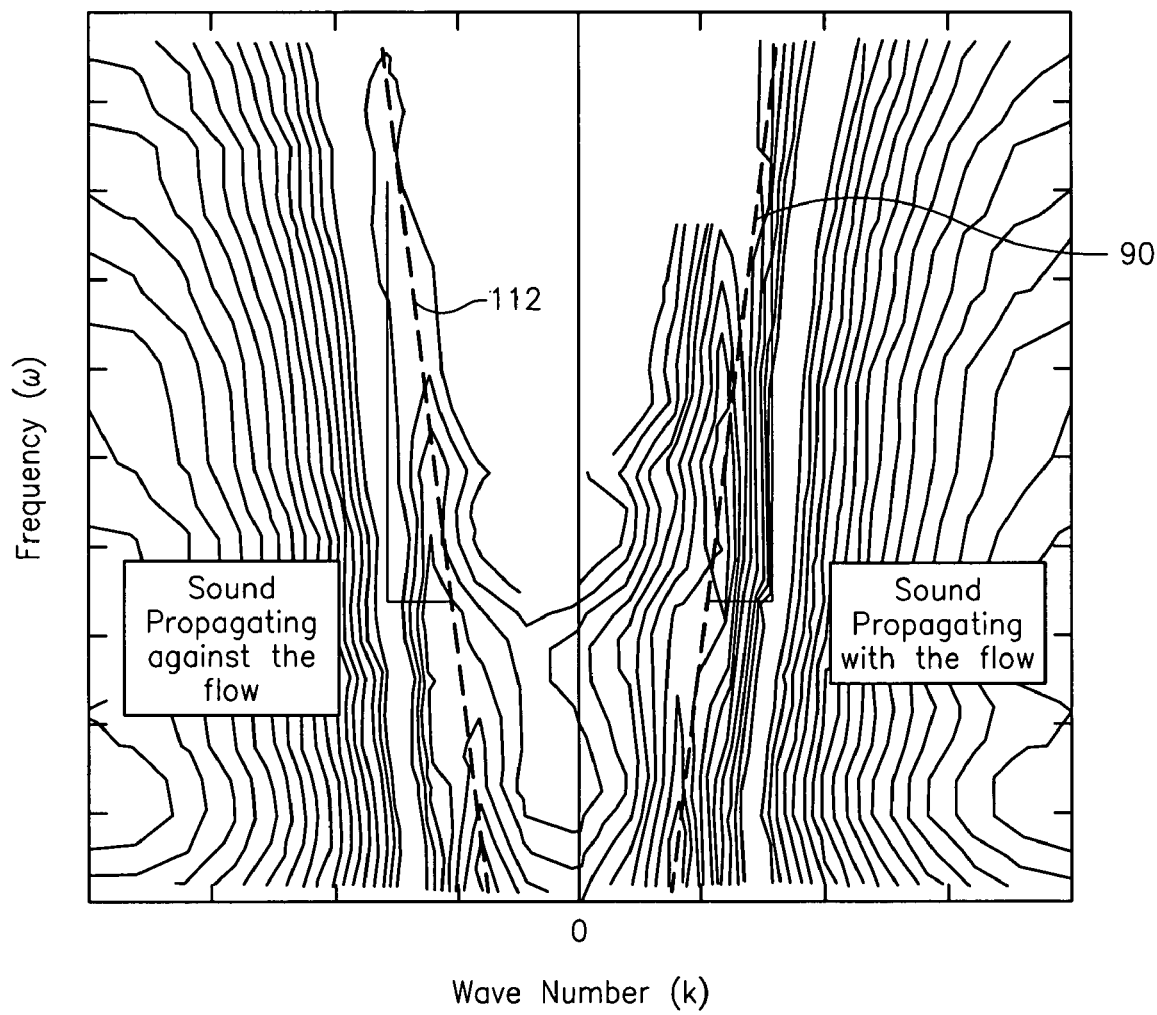
FIG. 17 is a kω plot of data processed from an array of pressure sensors use to measure the speed of sound of a fluid flow passing in a pipe, in accordance with the present invention.

In the case of suitable acoustic waves being present in both axial directions, the power in the k-ω plane shown in a k-ω plot of FIG. 17 so determined will exhibit a structure that is called an acoustic ridge 170,172 in both the left and right planes of the plot, wherein one of the acoustic ridges 170 is indicative of the speed of sound traveling in one axial direction and the other acoustic ridge 172 being indicative of the speed of sound traveling in the other axial direction. The acoustic ridges represent the concentration of a stochastic parameter that propagates through the flow and is a mathematical manifestation of the relationship between the spatial variations and temporal variations described above. Such a plot will indicate a tendency for k-ω pairs to appear more or less along a line 170,172 with some slope, the slope indicating the speed of sound.

The power in the k-ω plane so determined is then provided to an acoustic ridge identifier 162, which uses one or another feature extraction method to determine the location and orientation (slope) of any acoustic ridge present in the left and right k-ω plane. The velocity may be determined by using the slope of one of the two acoustic ridges 170,172 or averaging the slopes of the acoustic ridges 170,172.

Finally, information including the acoustic ridge orientation (slope) is used by an analyzer 164 to determine the flow parameters relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

An array processor 160 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k = 2\pi/\lambda$ where λ is the wavelength of a spectral component, and corresponding angular frequencies given by $\omega = 2\pi v$.

One such technique of determining the speed of sound propagating through the flow 12 is using array processing techniques to define an acoustic ridge in the k-ω plane as shown in FIG. 17. The slope of the acoustic ridge is indicative of the speed of sound propagating through the flow 12. The speed of sound (SOS) is determined by applying sonar arraying processing techniques to determine the speed at which the one dimensional acoustic waves propagate past the axial array of unsteady pressure measurements distributed along the pipe 14.

The apparatus 200 of the present invention measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and flow 12 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While the sonar-based flow meter using an array of sensors 118–121 to measure the speed of sound of an acoustic wave propagating through the mixture is shown and described, one will appreciate that any means for measuring the speed of sound of the acoustic wave may used to determine the entrained gas volume fraction of the mixture/fluid or other characteristics of the flow described hereinbefore.

The analyzer 164 of the processing unit 124 provides output signals indicative of characteristics of the process flow 12 that are related to the measured speed of sound (SOS) propagating through the flow 12. For example, to determine the gas volume fraction (or phase fraction), the analyzer 164 assumes a nearly isothermal condition for the flow 12. As such the gas volume fraction or the void fraction is related to the speed of sound by the following quadratic equation:

$$Ax^2 + Bx + C = 0$$

wherein x is the speed of sound, $A = 1 + rg/rl*(K_{eff}/P - 1) - K_{eff}/P$, $B = K_{eff}/P - 2 + rg/rl$; $C = 1 - K_{eff}/rl*a_{meas}^2$); Rg=gas density, rl=liquid density, $K_{eff}$=effective K (modulus of the liquid and pipewall), P=pressure, and $a_{meas}$=measured speed of sound.

Effectively,

Gas Voulume Fraction (GVF)=$(-B+\text{sqrt}(B^2-4*A*C))/(2*A)$

Alternatively, the sound speed of a mixture can be related to volumetric phase fraction ($\phi_i$) of the components and the sound speed (a) and densities ($\rho$) of the component through the Wood equation.

$$\frac{1}{\rho_{mix}a_{mix\infty}^2} = \sum_{i=1}^{N} \frac{\phi_i}{\rho_i a_i^2} \quad \text{where} \quad \rho_{mix} = \sum_{i=1}^{N} \rho_i \phi_i$$

One dimensional compression waves propagating within a flow 12 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{1/a_{mix\infty}^2 + \rho_{mix}\frac{2R}{Et}}} \quad \text{(eq 1)}$$

Figure 18:
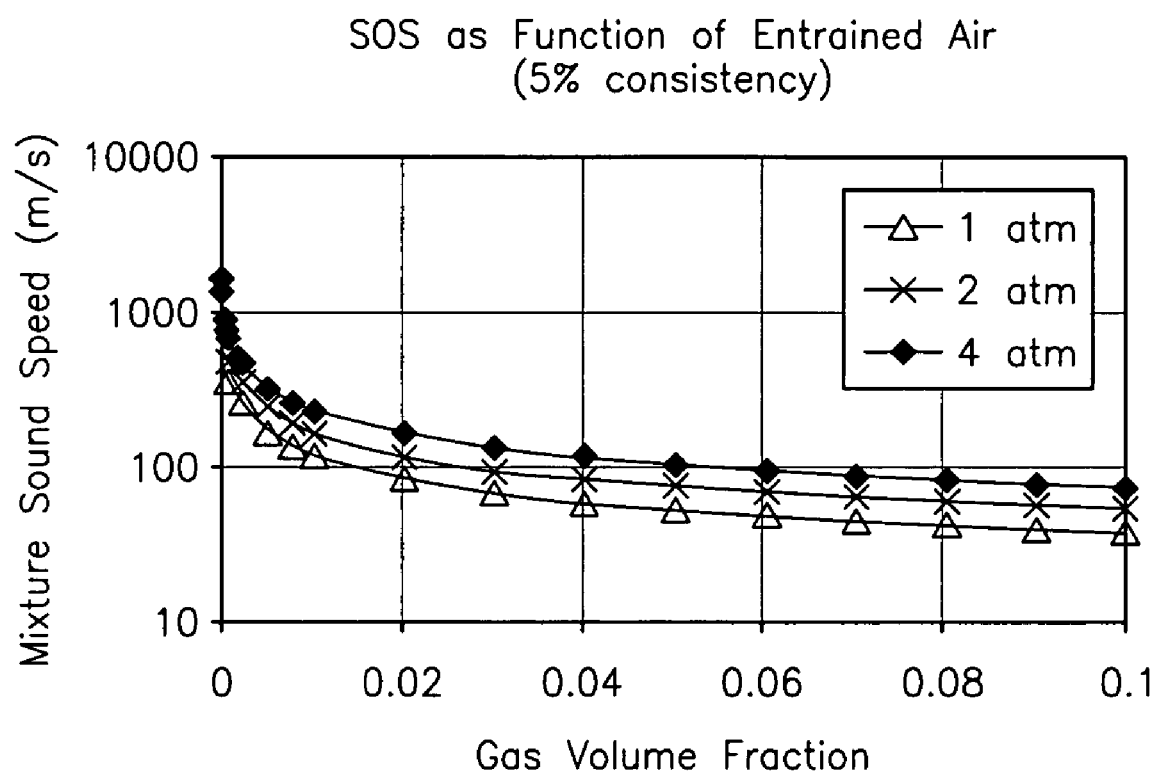
FIG. 18 is a plot of the speed of sound of the fluid flow as a function of the gas volume fraction over a range of different pressures, in accordance with the present invention.

The mixing rule essentially states that the compressibility of a mixture ($1/(\rho a^2)$) is the volumetrically-weighted average of the compressibilities of the components. For gas/liquid mixtures 12 at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained air volume fraction is shown in FIG. 18.

Some or all of the functions within the processing unit 24 may be implemented in software (using a microprocessor or computer) and/or firmware, or may be implemented using analog and/or digital hardware, having sufficient memory, interfaces, and capacity to perform the functions described herein.

Figure 20:
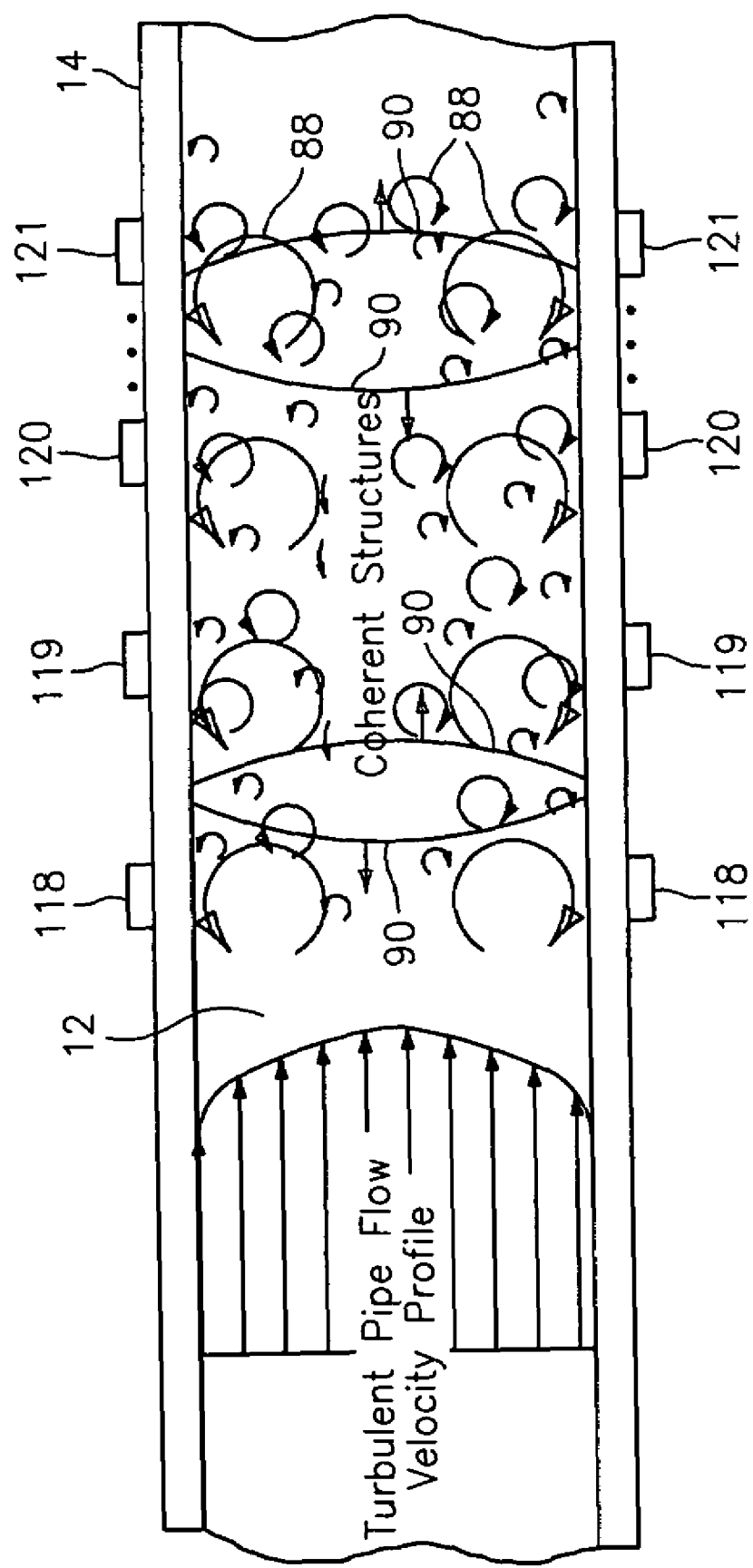
FIG. 20 is a graphical cross-sectional view of the fluid flow propagating through a pipe, in accordance with the present invention.
Figure 21:
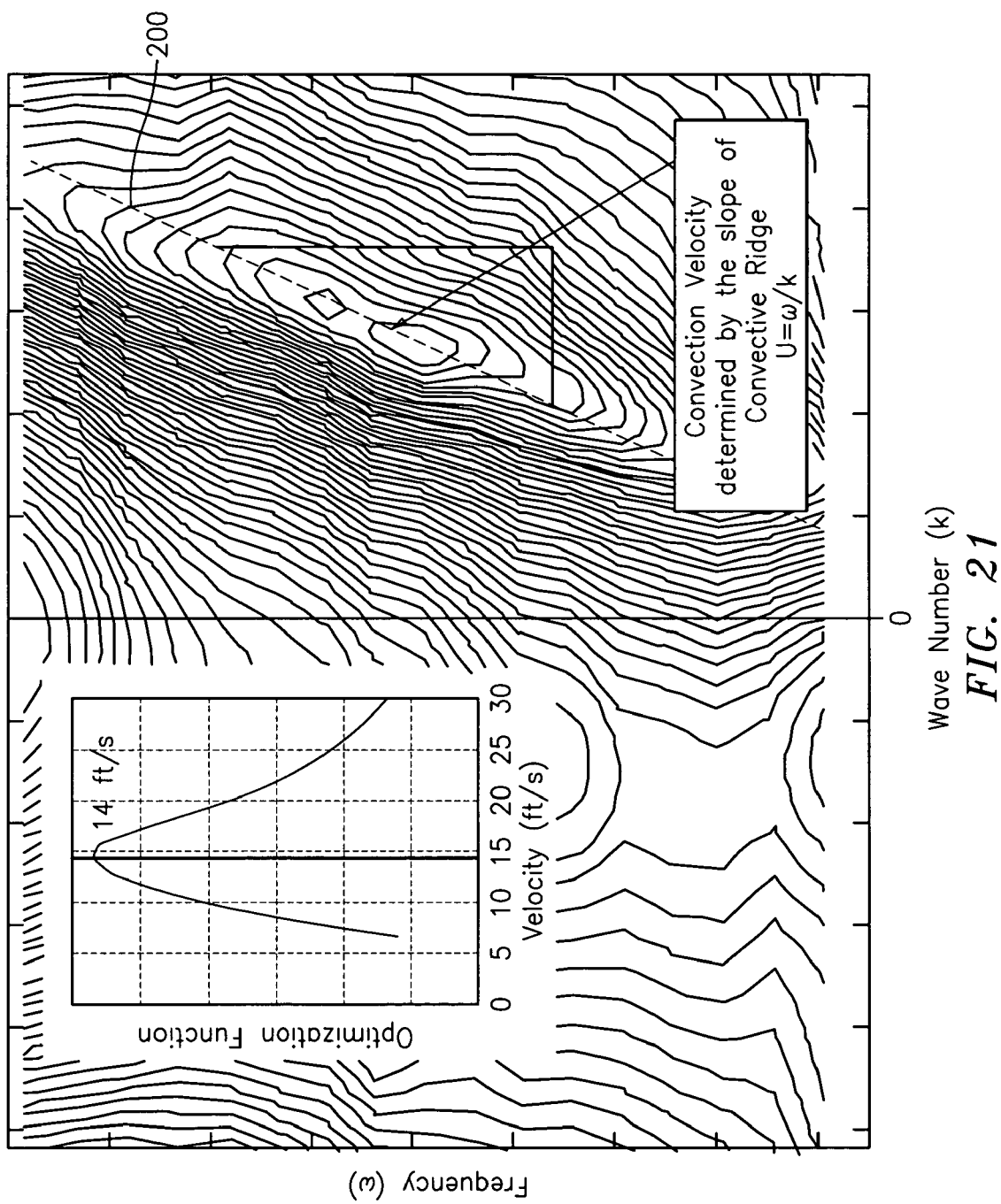
FIG. 21 is a kω plot of data processed from an array of pressure sensors use to measure the velocity of a fluid flow passing in a pipe, in accordance with the present invention.

While the embodiments of the present invention shown in FIGS. 2, 20 and 21 shown the pressure sensors 118–121 disposed on the pipe 14, separate from the coriolis meter, the present invention contemplates that the GVF meter 100 may be integrated with the coriolis meter to thereby provide a single apparatus. In this integrated embodiment, the pressure sensors 118–121 may be disposed on one or both of the tubes of the coriolis meter.

Figure 19:
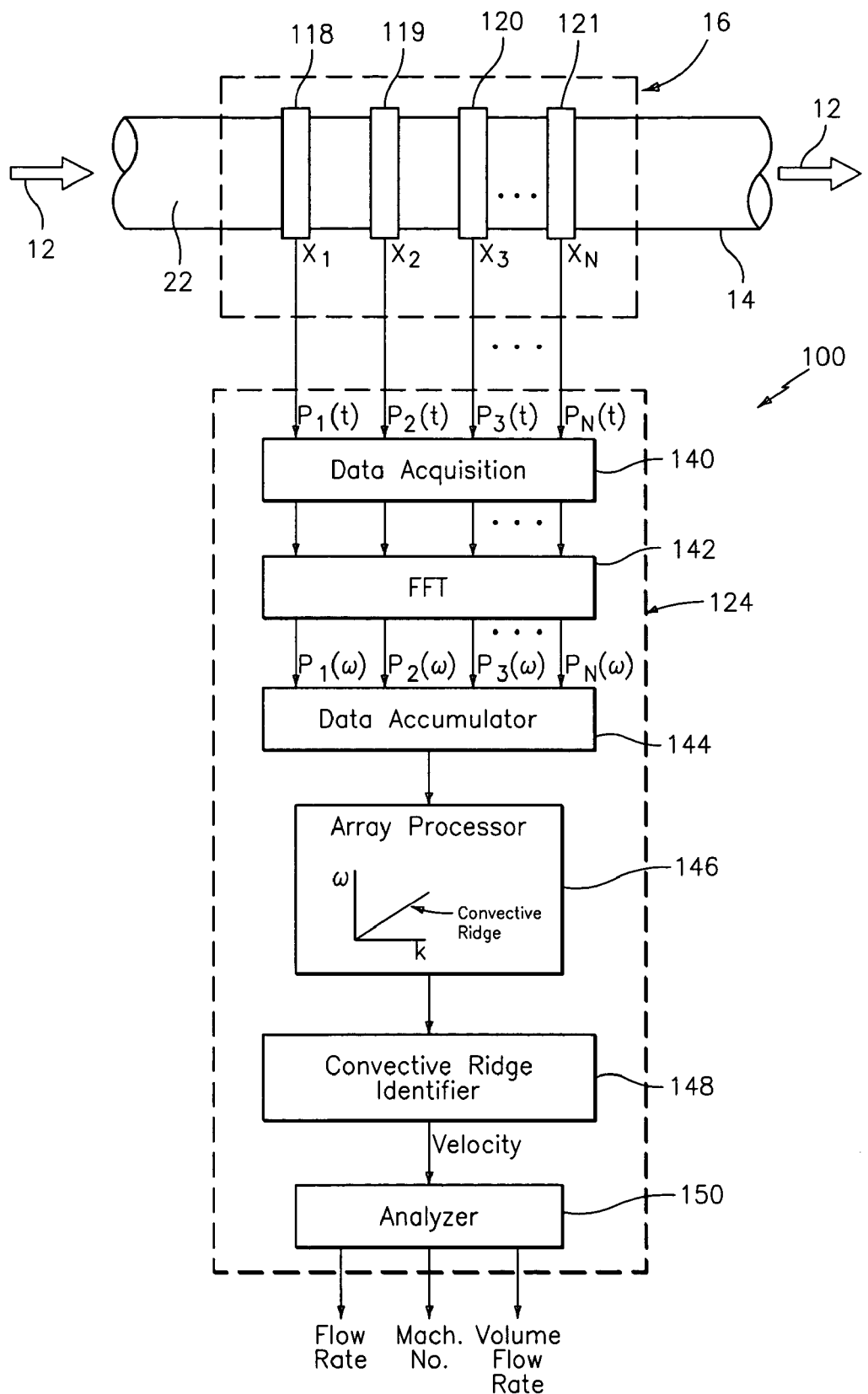
FIG. 19 is a schematic block diagram of a volumetric flow meter having an array of sensor, in accordance with the present invention.

As shown in FIG. 19, the flow meter 100 may process the array of pressure signals to determine the velocity and/or the volumetric flow of fluid flow 12. The flow meter 100 embodying the present invention has an array of at least two pressure sensors 118,119, located at two locations $x_1, x_2$ axially along the pipe 14 for sensing respective stochastic signals propagating between the sensors 118,119 within the pipe at their respective locations. Each sensor 118,119 provides a signal indicating an unsteady pressure at the location of each sensor, at each instant in a series of sampling instants. One will appreciate that the sensor array may include more than two pressure sensors as depicted by pressure sensor 120,121 at location $x_3$, $x_N$. The pressure generated by the convective pressure disturbances (e.g., eddies 88, see FIG. 20) may be measured through strained-based sensors and/or pressure sensors 118–121. The pressure sensors 118–121 provide analog pressure time-varying signals $P_1(t), P_2(t), P_3(t), P_N(t)$ to the signal processing unit 124. The processing unit 24 processes the pressure signals to first provide output signals indicative of the pressure disturbances that convect with the flow 12, and subsequently, provide output signals in response to pressure disturbances generated by convective waves propagating through the flow 12, such as velocity, Mach number and volumetric flow rate of the process flow 12.

The processing unit 24 receives the pressure signals from the array of sensors 118–121. A data acquisition unit 140 (e.g., A/D converter) converts the analog signals to respective digital signals. The FFT logic calculates the Fourier transform of the digitized time-based input signals $P_1(t)$–$P_N$ (t) and provides complex frequency domain (or frequency based) signals $P_1(\omega), P_2(\omega), P_3(\omega), P_N(\omega)$ indicative of the frequency content of the input signals. Instead of FFT's, any other technique for obtaining the frequency domain characteristics of the signals $P_1(t)$–$P_N(t)$, may be used. For example, the cross-spectral density and the power spectral density may be used to form a frequency domain transfer functions (or frequency response or ratios) discussed hereinafter.

One technique of determining the convection velocity of the turbulent eddies 88 within the process flow 12 is by characterizing a convective ridge of the resulting unsteady pressures using an array of sensors or other beam forming techniques, similar to that described in U.S. patent application Ser. No. 10/007,736 and U.S. patent application 6,889, 562, Ser. No. 09/729,994, filed Dec. 4, 200, now U.S. Pat. No. 6,609,069, which are incorporated herein by reference.

A data accumulator 144 accumulates the frequency signals $P_1(\omega)$–$P_N(\omega)$ over a sampling interval, and provides the data to an array processor 146, which performs a spatial-temporal (two-dimensional) transform of the sensor data, from the xt domain to the k-ω domain, and then calculates the power in the k-ω plane, as represented by a k-ω plot.

The array processor 146 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where λ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length.

Convective characteristics or parameters have a dispersion relationship that can be approximated by the straight-line equation, $k=\omega/u,$ where u is the convection velocity (flow velocity). A plot of k-ω pairs obtained from a spectral analysis of sensor samples associated with convective parameters portrayed so that the energy of the disturbance spectrally corresponding to pairings that might be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 88 is distributed over a range of length scales and hence temporal frequencies.

To calculate the power in the k-ω plane, as represented by a k-ω plot (see FIG. 21) of either the signals, the array processor 146 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 118–121.

The present invention may use temporal and spatial filtering to precondition the signals to effectively filter out the common mode characteristics $P_{common\ mode}$ and other long wavelength (compared to the sensor spacing) characteristics in the pipe 14 by differencing adjacent sensors and retain a substantial portion of the stochastic parameter associated with the flow field and any other short wavelength (compared to the sensor spacing) low frequency stochastic parameters.

In the case of suitable turbulent eddies 88 (see FIG. 20) being present, the power in the k-ω plane shown in a k-ω plot of FIG. 21 shows a convective ridge 200. The convective ridge represents the concentration of a stochastic parameter that convects with the flow and is a mathematical manifestation of the relationship between the spatial variations and temporal variations described above. Such a plot will indicate a tendency for k-ω pairs to appear more or less along a line 200 with some slope, the slope indicating the flow velocity.

Once the power in the k-ω plane is determined, a convective ridge identifier 148 uses one or another feature extraction method to determine the location and orientation (slope) of any convective ridge 200 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 148 provides information about the different trial convection velocities, information referred to generally as convective ridge information.

The analyzer 150 examines the convective ridge information including the convective ridge orientation (slope). Assuming the straight-line dispersion relation given by k=ω/u, the analyzer 150 determines the flow velocity, Mach number and/or volumetric flow. The volumetric flow is determined by multiplying the cross-sectional area of the inside of the pipe with the velocity of the process flow.

For any embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe if desired.

It is also within the scope of the present invention that any other strain sensing technique may be used to measure the variations in strain in the pipe, such as highly sensitive piezoelectric, electronic or electric, strain gages attached to or embedded in the pipe. Accelerometers may be also used to measure the unsteady pressures. Also, other pressure sensors may be used, as described in a number of the aforementioned patents, which are incorporated herein by reference.

In another embodiment, the sensor may comprise of piezofilm or strips (e.g. PVDF) as described in at least one of the aforementioned patent applications.

While the illustrations show four sensors mounted or integrated in a tube of the coriolis meter, the invention contemplates any number of sensors in the array as taught in at least one of the aforementioned patent applications. Also the invention contemplates that the array of sensors may be mounted or integrated with a tube of a coriolis meter having shape, such as pretzel shape, U-shaped (as shown), straight tube and any curved shape.

The invention further contemplated providing an elongated, non-vibrating (or oscillating) portion that permits a greater number of sensors to be used in the array.

While the present invention describes an array of sensors for measuring the speed of sound propagating through the flow for use in interpreting the relationship between coriolis forces and the mass flow through a coriolis meter. Several other methods exists.

For example, for a limited range of fluids, an ultrasonic device could be used to determine speed of sound of the fluid entering. It should be noted that the theory indicates that the interpretation of coriolis meters will be improved for all fluids if the sound speed of the process fluid is measured and used in the interpretation. Thus, knowing that the sound speed of the fluid is 5000 ft/sec as it would be for a water like substance, compared to 1500 ft/sec as it would be for say supercritical ethylene, would improve the performance of a coriolis based flow and density measurement. These measurements could be performed practically using existing ultrasonic meters.

Another approach to determine speed of sound of the fluids is to measure the resonant frequency of the acoustic modes of the flow tubes. When installed in a flow line, the cross sectional area changes associated with the transition from the pipe into the typically much smaller flow tubes creates a significant change in acoustic impedance. As a result of this change in impedance, the flow tube act as somewhat of a resonant cavity. By tracking the resonant frequency of this cavity, one could determine the speed of sound of the fluid occupying the cavity. This could be performed with a single pressure sensitive device, mounted either on the coriolis meter, of on the piping network attached to the coriolis meter.

In a more general aspect, the present invention contemplates the ability to augmenting the performance of a coriolis meter using any method or means for measuring the gas volume fraction of the fluid flow.

In one embodiment of the present invention as shown in FIG. 20, each of the pressure sensors 118–121 may include a piezoelectric film sensor to measure the unsteady pressures of the fluid flow 12 using either technique described hereinbefore.

The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 14 due to unsteady pressure variations (e.g., acoustic waves) within the process mixture 12. Strain within the pipe is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. No. 10/712,818, U.S. patent application Ser. No. 10/712,833, and U.S. patent application Ser. No. 10/795,111, which are incorporated herein by reference.

Another embodiment of the present invention include a pressure sensor such as pipe strain sensors, accelerometers, velocity sensors or displacement sensors, discussed hereinafter, that are mounted onto a strap to enable the pressure sensor to be clamped onto the pipe. The sensors may be removable or permanently attached via known mechanical techniques such as mechanical fastener, spring loaded, clamped, clam shell arrangement, strapping or other equivalents. These certain types of pressure sensors, it may be desirable for the pipe 12 to exhibit a certain amount of pipe compliance.

Instead of single point pressure sensors 118–121, at the axial locations along the pipe 12, two or more pressure sensors may be used around the circumference of the pipe 12 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 118–121 of FIG. 20 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 118–121 may be Bragg grating based pressure sensors, such as that described in U.S. patent application, Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application, Ser. No. 10/224,821, entitled "Non-Intrusive Fiber Optic Pressure Sensor for Measuring Unsteady Pressures within a Pipe", which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 115–118 and it may measure the unsteady (or dynamic or ac) pressure variations inside the pipe or tube 14 by measuring the pressure levels inside of the tube. These sensors may be ported within the pipe to make direct contact with the mixture 12. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the tube, such as highly sensitive piezoelectric, electronic or electric, strain gages attached to or embedded in the tube 14.

While a number of sensor have been described, one will appreciate that any sensor the measures the speed of sound propagating through the fluid may be used with the present invention, including ultrasonic sensors.

The coriolis meter described herein before may be any known coriolis meter, such as two inch bent tube coriolis meter manufactured my MicroMotion Inc. and a two in straight tube coriolic meter manufactured by Endress & Hauser Inc. The coriolis meters comprise a pair of bent tubes (e.g. U-shaped, pretzel shaped) or straight tubes.

While a particular density meter was described for an embodiment, the present invention contemplates any density meter may be used in the embodiments. Similarly, while a particular meter was provided to determine speed of sound propagating through the fluid flow 12, the present invention contemplates any SOS measuring device may be used.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. A flow measuring system for determining the density of an aerated fluid flowing in a pipe, the flow measuring system comprising:
   a density meter that provides a density signal indicative of the density of the fluid flowing in the pipe;
   a flow measuring device including at least one sensor that measures the speed of sound propagating through the fluid, the flow measuring device providing an SOS signal indicative of the speed of sound propagating through the fluid and/or a GVF signal indicative of the gas volume fraction of the fluid; and
   a processing unit that determines the density of the non-gaseous component of the aerated fluid in response to the SOS signal and/or the GVF signal and the density signal.

2. The flow measuring system of claim 1, wherein the speed of sound measurement is used to determine a gas volumetric fraction (GVF) in the flow of the fluid.

3. The flow measuring system of claim 1, wherein the density meter includes one of a nuclear densitometer, a vibrating vane densitometer and a coriolis meter.

4. The flow measuring system of claim 1, wherein the at least one sensor includes at least two pressure strain sensors at different axial locations along the pipe, each of the pressure strain sensors providing a respective pressure strain signal indicative of an acoustic pressure disturbance within the pipe at a corresponding axial position.

5. The flow measuring system of claim 1, wherein the at least one sensor includes 2, 3, 4, 5, 6, 7, 8, 9, 10, 11, 12, 13, 14, 15, or 16 strain based sensors disposed axially along the pipe.

6. The flow measuring system of claim 1, wherein the gas volume fraction is determined using the following formula:

$$\text{Gas Voulume Fraction} = (-B + \sqrt{B^2 - 4*A*C})/(2*A)$$

wherein $A = 1rg/rl*(K_{eff}/P - 1) - K_{eff}/P$, $B = K_{eff}/P - 2 + rg/rl$; $C = 1 - K_{eff}/rl*a_{meas}^2$; Rg=gas density, rl=liquid density, $K_{eff}$ effective K (modulus of the liquid and pipewall), P=pressure, and $a_{meas}$=measured speed of sound.

7. The flow measuring system of claim 1, wherein the processing unit determines a slope of an acoustic ridge in the k-ω plane, in response to the pressure signals, to provide a SOS signal indicative of the speed of sound propagating through the fluid.

8. The flow measuring system of claim 1, wherein the density of the non-gaseous components of the fluid is determined using the following equation:

$$\rho_{nongas} = \rho_{mix}/(1 - \phi_{gas})$$

wherein $\rho_{mix}$ is the density of the mixture, $\rho_{nongas}$, $\emptyset_{nongas}$ are the density and phase fraction, respectively, of a non-gas component of the fluid flow, and $\rho_{gas}$, $\emptyset_{gas}$ are the density and phase fraction, respectively, of the entrained gas within the mixture.

9. The flow measuring system of claim 1, wherein the speed of sound is associated with acoustic waves that are one dimensional acoustic waves propagating axially through the pipe.

10. The flow measuring system of claim 9, wherein the acoustic waves are passive noise.

11. The flow measuring system of claim 1, wherein the processor provides a signal indicative of the volumetric phase fraction of the non-gaseous components of the fluid, wherein the non-gaseous components comprise two components.

12. The flow measuring system of claim 11, wherein the non-gaseous components of the fluid consist of liquid/liquid components or liquid/solid components of the fluid.

13. The flow measuring system of claim 11, wherein the volumetric phase fraction of each of the non-gaseous components of the fluid is determined solving the following equations:

$$\rho_{mix} = \rho_1\phi_1 + \rho_2\phi_2 + \rho_{gas}\phi_{gas}; \text{ and}$$

$$\phi_{gas} + \phi_1 + \phi_2 = 1$$

wherein $\rho_{mix}$ is the density of the mixture, $\rho_1$, $\rho_2$ are the density of two non-gaseous components of the fluid, and $\emptyset_1$, $\emptyset_2$ are the phase fraction of two non-gaseous components of the fluid, and $\rho_{gas}$, $\emptyset_{gas}$ are the density and phase fraction, respectively, of the entrained gas within the fluid.

14. The flow measuring system of claim 1, wherein the flow measuring device comprises an array of sensors disposed axially along the pipe for measuring acoustic pressures in the fluid, and providing respective pressure signals.

15. The flow measuring system of claim 14, wherein the array of sensors includes at least one of strain based sensors, pressure sensors, ported pressure sensors and ultra-sonic sensors.

16. A method for determining the density of an aerated fluid flowing in a pipe, the method comprising:
providing a density signal indicative of the density of the fluid flowing in the pipe;
providing an SOS signal indicative of the speed of sound propagating through the fluid and/or a GVF signal indicative of the gas volume fraction of the fluid; and
determining the density of the non-gaseous component of the aerated fluid in response to the SOS signal and/or the GVF signal and the density signal.

17. The method of claim 16, further includes determining the GVF signal in response to the SOS signal.

18. The method of claim 16, further includes determining the GVF signal using the following formula:

$$\text{Gas Voulume Fraction} = (-B + \sqrt{B^2 - 4*A*C})/(2*A)$$

wherein $A = 1rg/rl*(K_{eff}/P - 1) - K_{eff}/P$, $B = K_{eff}/P - 2 + rg/rl$; $C = 1 - K_{eff}/rl*a_{meas}^2$; Rg=gas density, rl=liquid density, $K_{eff}$ effective K (modulus of the liquid and pipewall), P=pressure, and $a_{meas}$=measured speed of sound.

19. The method of claim 16, wherein determining the density of the non-gaseous components of the fluid is determined using the following equation:

$$\rho_{nongas} = \rho_{mix}/(1 - \phi_{gas})$$

wherein $\rho_{mix}$ is the density of the mixture, $\rho_{nongas}$, $\emptyset_{nongas}$ are the density and phase fraction, respectively, of a non-gas component of the fluid flow, and $\rho_{gas}$, $\emptyset_{gas}$ are the density and phase fraction, respectively, of the entrained gas within the mixture.

20. The method of claim 16, further includes measuring the density of the fluid to provide the density signal.

21. The method of claim 16, wherein the speed of sound is associated with acoustic waves that are one dimensional acoustic waves propagating axially through the pipe.

22. The method of claim 21, wherein the sound waves are passive noise.

23. The method of claim 16, further includes providing a signal indicative of the volumetric phase fraction of the non-gaseous components of the fluid, wherein the non-gaseous components comprise two components.

24. The method of claim 23, wherein the non-gaseous components of the fluid consist of liquid/liquid components or liquid/solid components of the fluid.

25. The method of claim 23, wherein the volumetric phase fraction of each of the non-gaseous components of the fluid is determined salving the following equations:

$$\rho_{mix} = \rho_1\phi_1 + \rho_2\phi_2 + \rho_{gas}\phi_{gas}; \text{ and}$$

$$\phi_{gas} + \phi_1 + \phi_2 = 1$$

wherein $\rho_{mix}$ is the density of the mixture, $\rho_1$, $\rho_2$ are the density of two non-gaseous components of the fluid, and $\emptyset_1$, $\emptyset_2$ are the phase fraction of two non-gaseous components of the fluid, and $\rho_{gas}$, $\rho_{gas}$ are the density and phase fraction, respectively, of the entrained gas within the fluid.

26. The method of claim 20, further includes using one of a nuclear densitometer, a vibrating vane densitometer and a coriolis meter to measure the density of the fluid.

27. The method of claim 16, further includes measuring the speed of sound propagating through the fluid to provide the SOS signal indicative of the speed of sound propagating through the fluid and/or the GVF signal indicative of the gas volume fraction of the fluid.

28. The method of claim 27, wherein measuring the speed of sound includes using an array of sensors disposed axially along the pipe for measuring acoustic pressures in the fluid and providing respective pressure signals.

29. The method of claim 28, wherein determining the SOS signal and/or GVF signal includes determining a slope of an acoustic ridge in the k-ω plane, in response to the pressure signals, to provide a SOS signal indicative of the speed of sound propagating through the fluid.

30. The method claim 28, wherein the array of sensors includes at least one of strain based sensors, pressure sensors, ported pressure sensors and ultra-sonic sensors.

31. The method of claim 28, wherein the array of sensors includes at least two pressure strain sensors at different axial locations along the pipe, each of the pressure strain sensors providing a respective pressure strain signal indicative of an acoustic pressure disturbance within the pipe at a corresponding axial position.

32. The method of claim 28, wherein the array of sensors includes 3, 4, 5, 6, 7, 8, 9, 10, 11, 12, 13, 14, 15, or 16 strain based sensors disposed axially along the pipe.

* * * * *